United States Patent [19]

Gleave et al.

[11] Patent Number: 5,660,727

[45] Date of Patent: Aug. 26, 1997

[54] AUTOMATED ANALYTE SUPERCRITICAL FLUID EXTRACTION APPARATUS

[75] Inventors: Gary L. Gleave, Milpitas; Norman J. Rothe, Foster City; David W. Kemp, San Jose, all of Calif.; Bruce E. Richter, Sandy; John L. Ezzell, Layton, both of Utah

[73] Assignee: Dionex Corporation, Sunnyvale, Calif.

[21] Appl. No.: 398,140

[22] Filed: Mar. 3, 1995

Related U.S. Application Data

[63] Continuation-in-part of Ser. No. 259,667, Jun. 14, 1994.

[51] Int. Cl.[6] .................... B01D 17/12; B01D 11/00; G01N 35/02; G01N 35/04
[52] U.S. Cl. ................... 210/141; 210/149; 210/198.2; 210/511; 210/634; 422/63; 422/64
[58] Field of Search .................. 422/64, 261, 63, 422/65, 69, 70; 210/634, 511, 198.2, 86, 97, 138, 141, 142, 143, 198.1, 205, 656, 94, 149, 175; 96/101, 103, 106

[56] References Cited

U.S. PATENT DOCUMENTS

| | | |
|---|---|---|
| 3,418,084 | 12/1968 | Allington . |
| 4,168,955 | 9/1979 | Allington et al. ............... 422/65 |
| 4,335,620 | 6/1982 | Adams et al. ................... 422/64 |
| 4,429,584 | 2/1984 | Beyer et al. ..................... 422/64 |
| 5,132,014 | 7/1992 | Allington . |
| 5,133,859 | 7/1992 | Frank et al. .................... 210/656 |
| 5,160,624 | 11/1992 | Clay . |
| 5,173,188 | 12/1992 | Winter . |
| 5,198,197 | 3/1993 | Clay . |
| 5,205,987 | 4/1993 | Ashraf-Khorassani . |
| 5,250,195 | 10/1993 | Winter . |
| 5,268,102 | 12/1993 | Clay et al. ...................... 210/634 |

*Primary Examiner*—Joseph W. Drodge
*Attorney, Agent, or Firm*—Flehr Hohbach Test Albritton & Herbert LLP

[57] ABSTRACT

An apparatus for automated extraction of an analyte from a sample positioned in a sample containment cell having a fluid passageway structure for communication of an extraction fluid to and from the cavity of the cell. The apparatus includes a loading tray, an oven assembly mounted proximate the loading tray, a fluid communication assembly mounted proximate the tray, a cell manipulation assembly and a controller. The cell manipulation assembly brings an inlet conduit and an outlet conduit of the fluid communication assembly into sealed relationship with the sample containment cell and uses the conduits to pick up and move the cell to and from the cell tray and oven assembly. The fluid communication assembly further causes flow of an extraction fluid into the cell and pressurizes the cell for extraction of an analyte from the sample under elevated temperatures and pressures, which can be under supercritical conditions for supercritical fluid extraction but preferably are below supercritical conditions for solvent extraction. The apparatus and method include a solvent extraction soak, purging of the extracted fluid, flushing with a gas and rinsing so as to avoid contamination of subsequent analyte extractions.

53 Claims, 11 Drawing Sheets

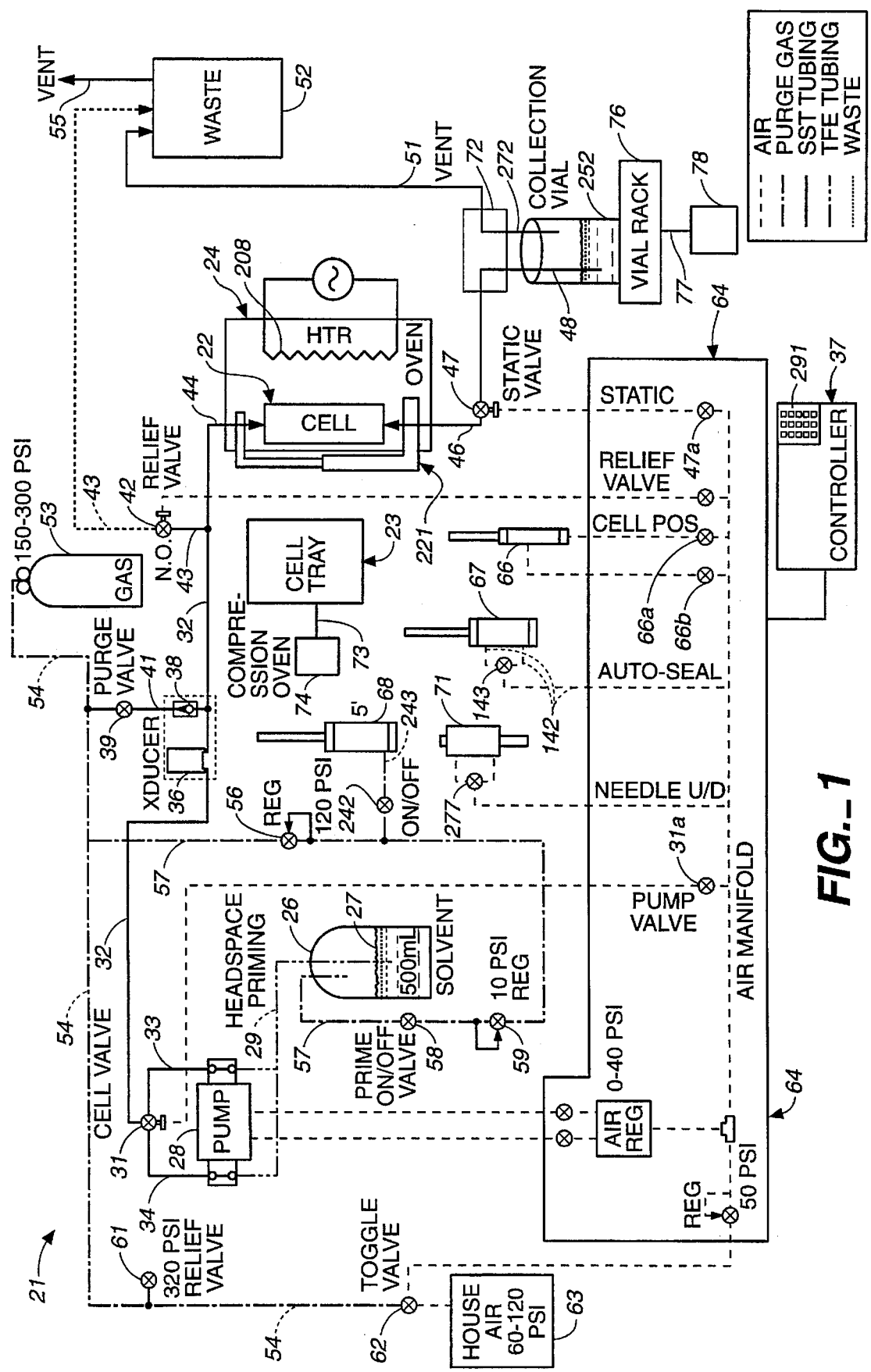
FIG._1

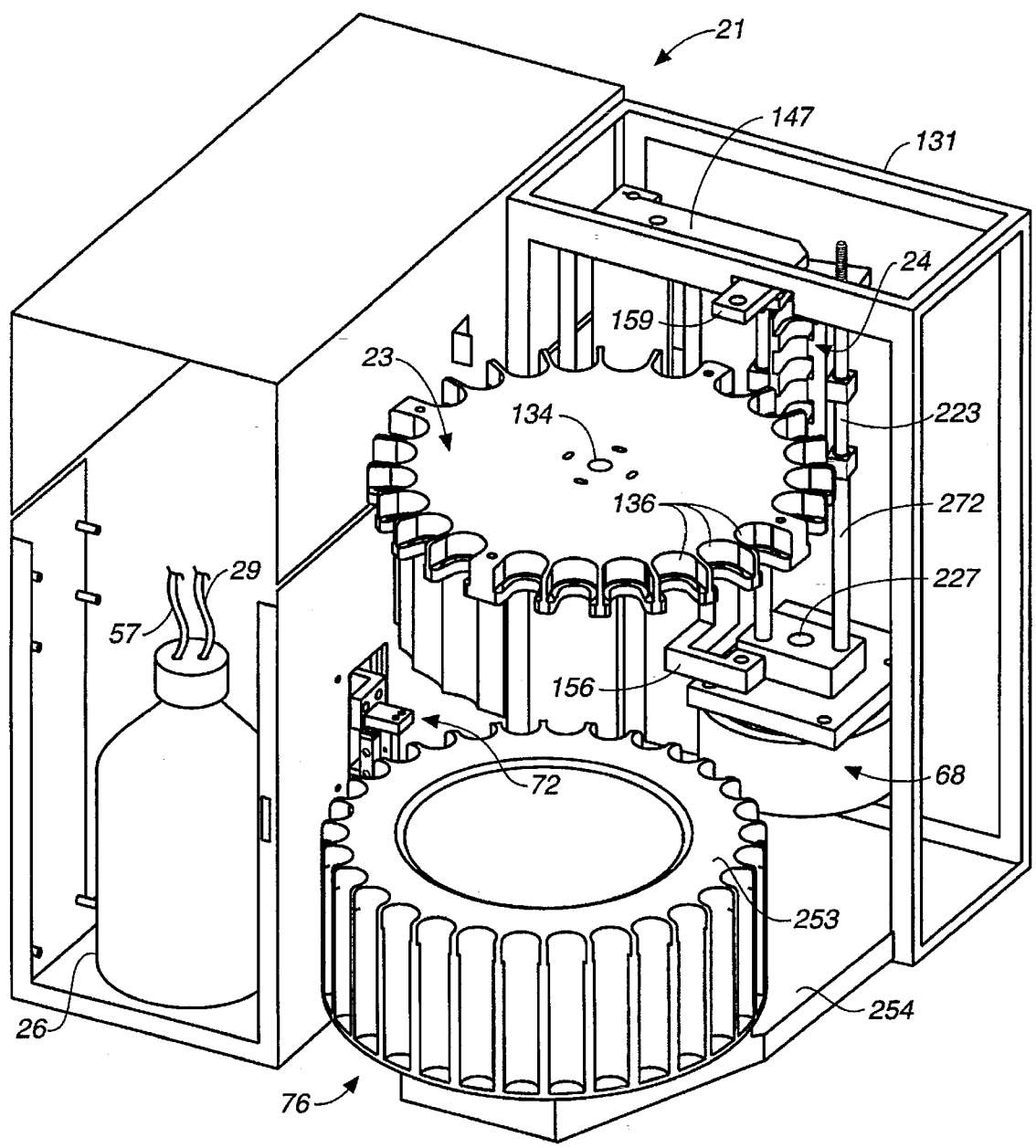
FIG._2

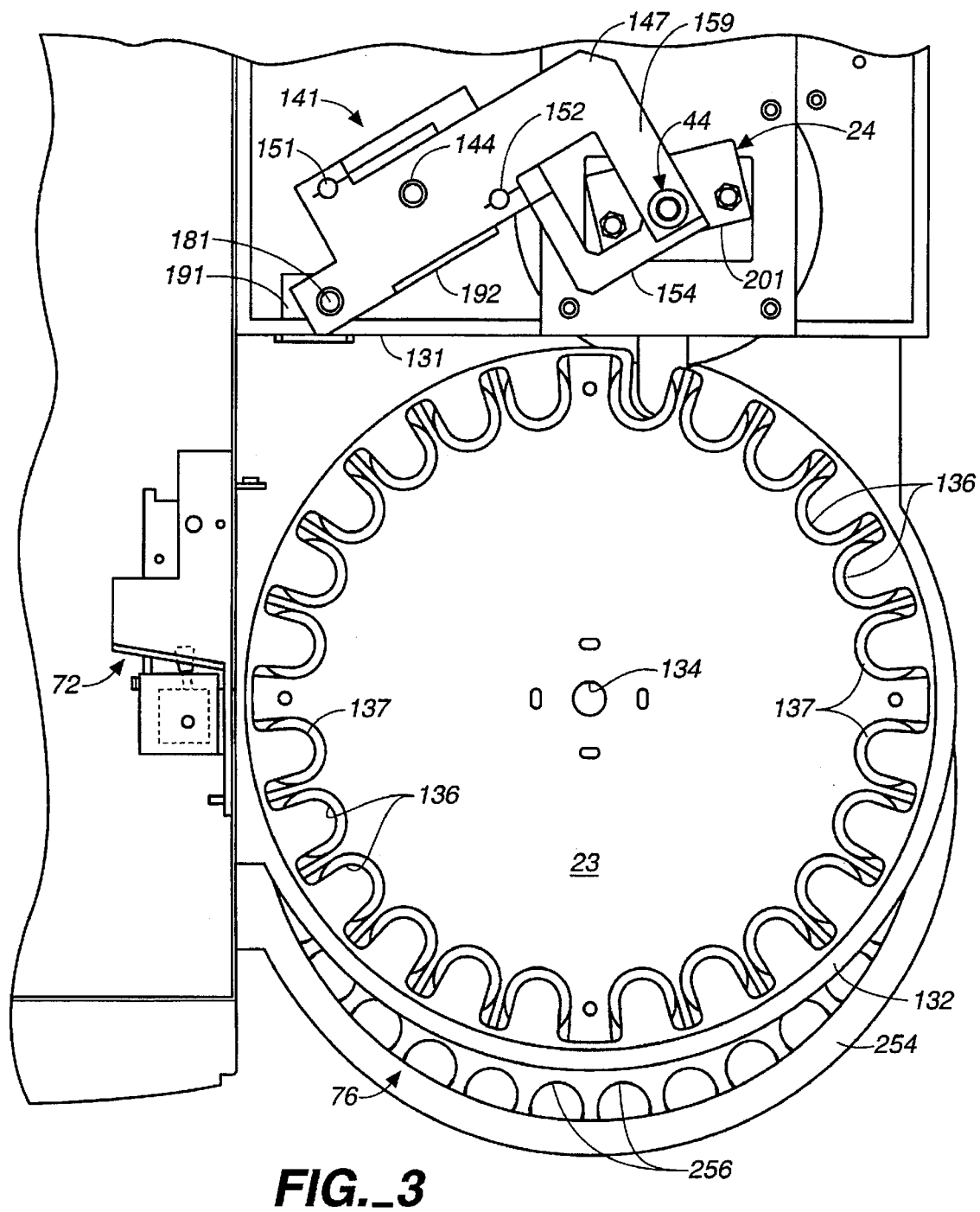
FIG._3

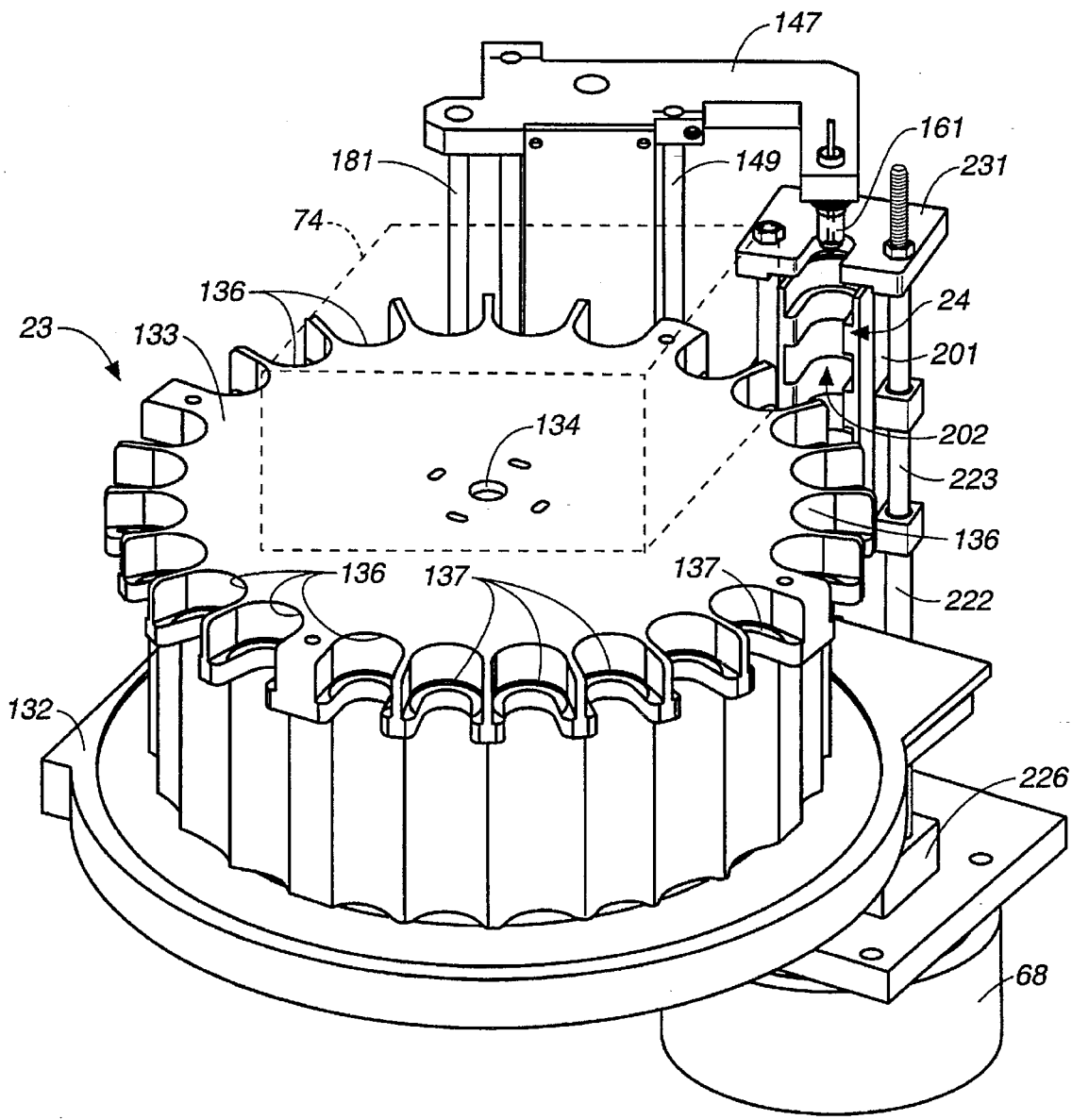
FIG._4

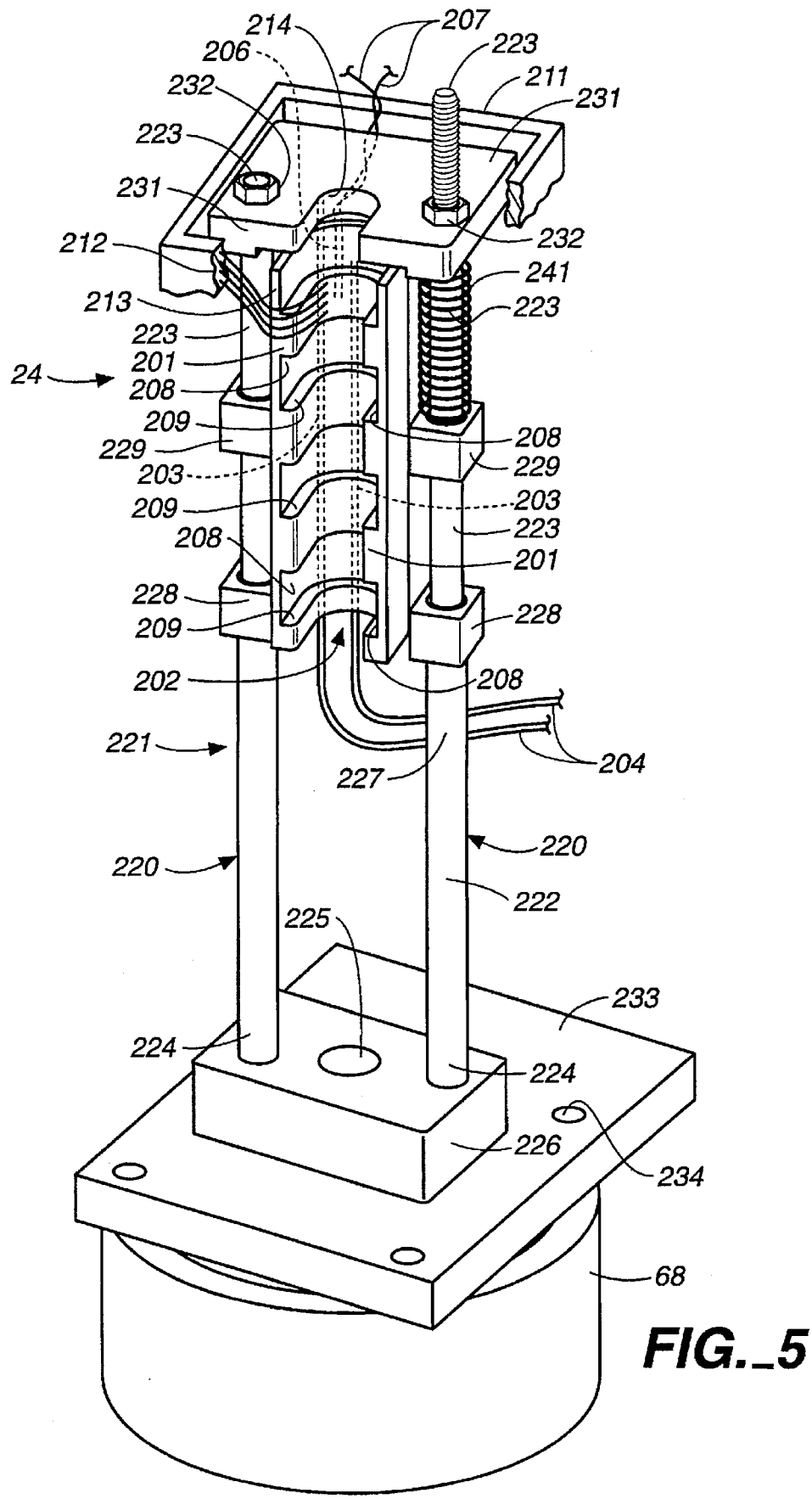
FIG._5

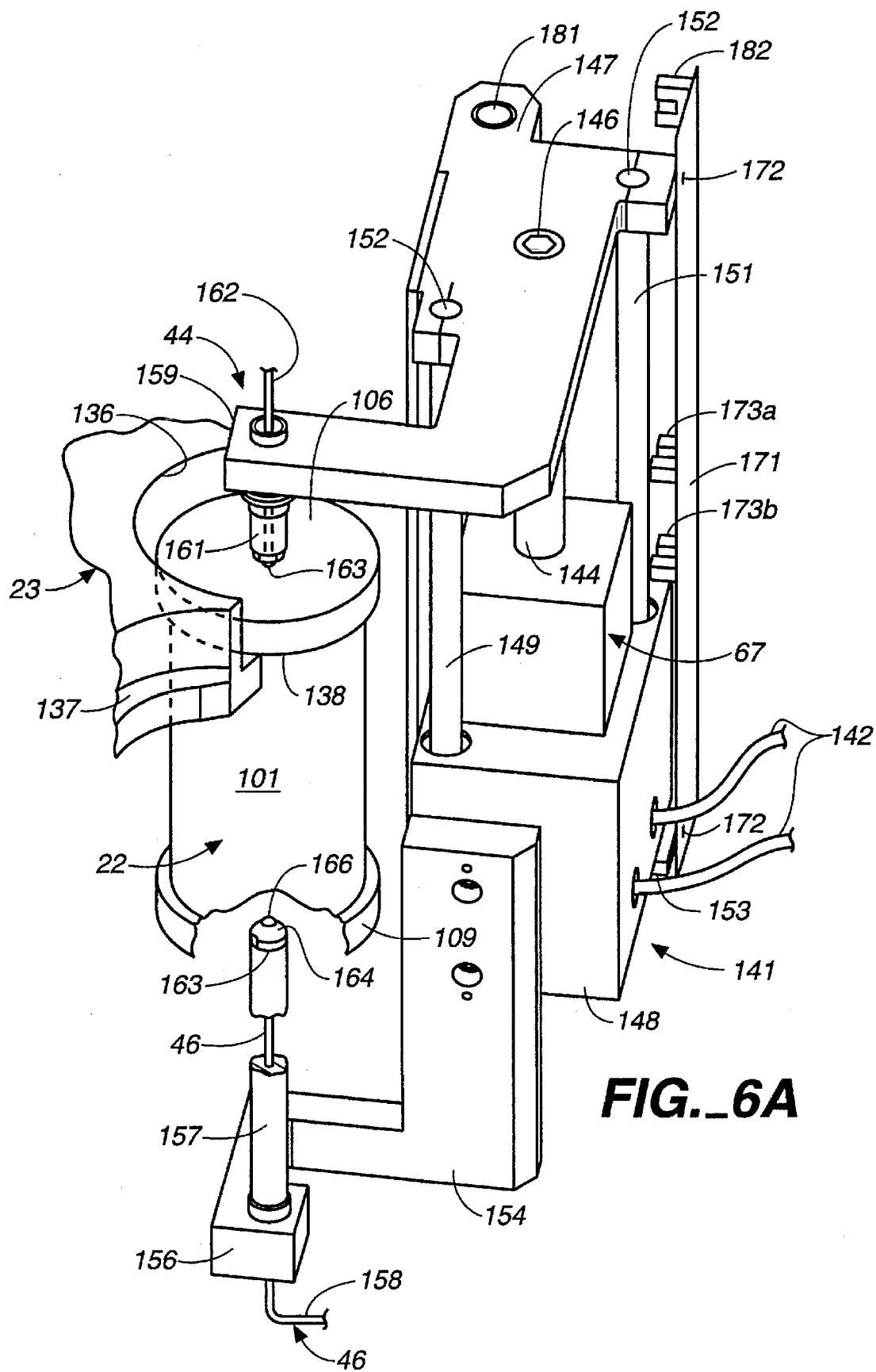
FIG._6A

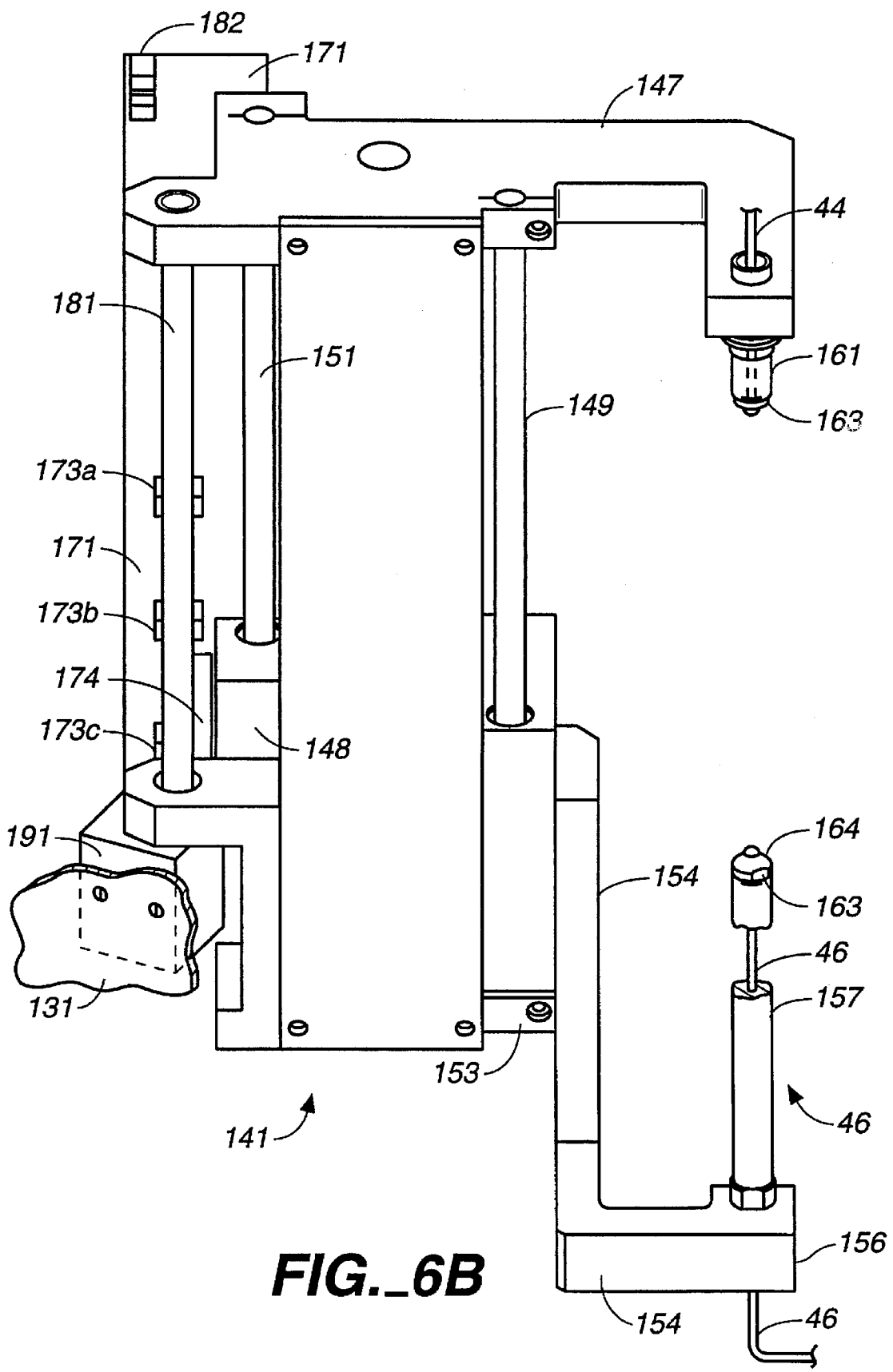
FIG._6B

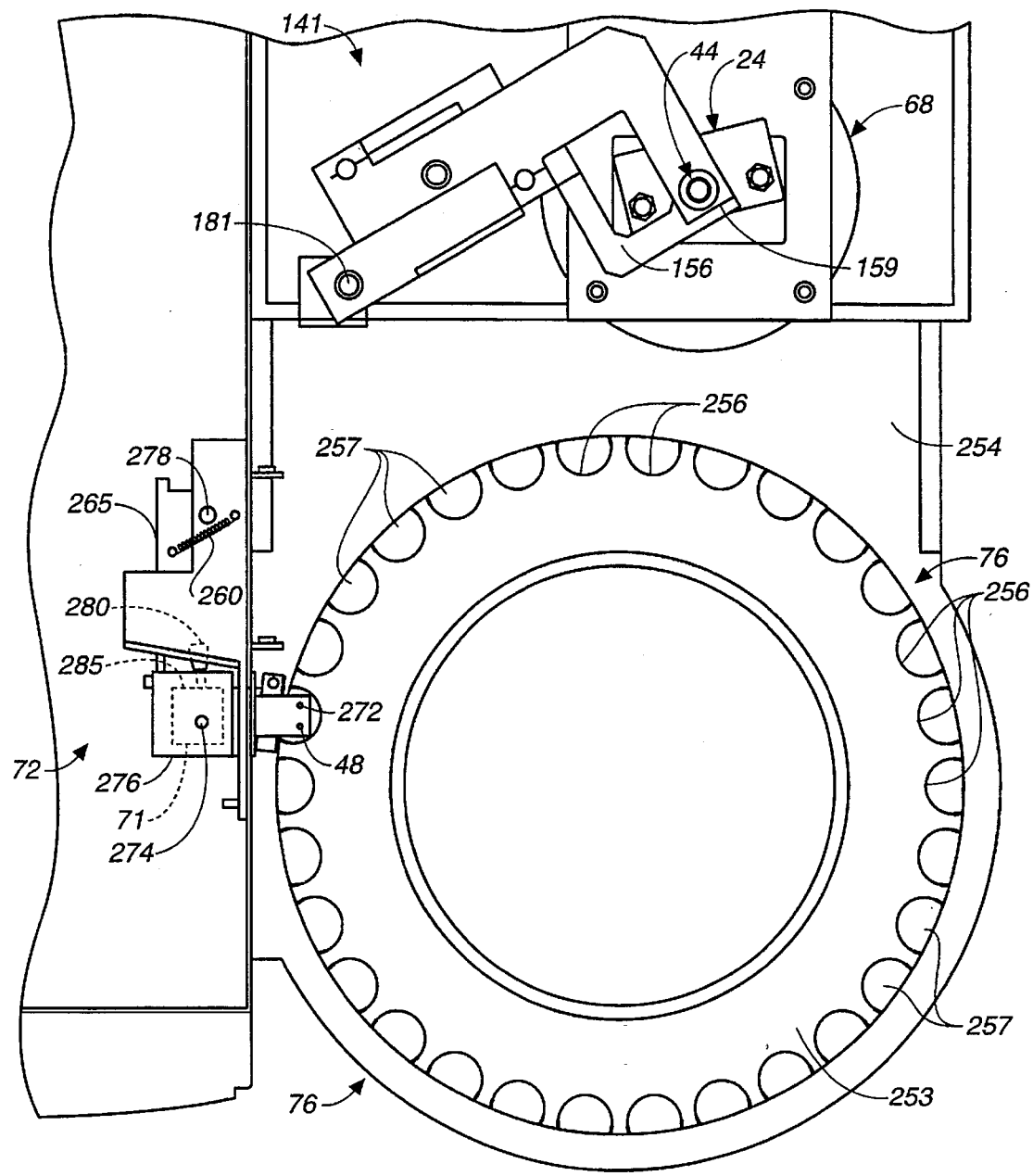
FIG._7

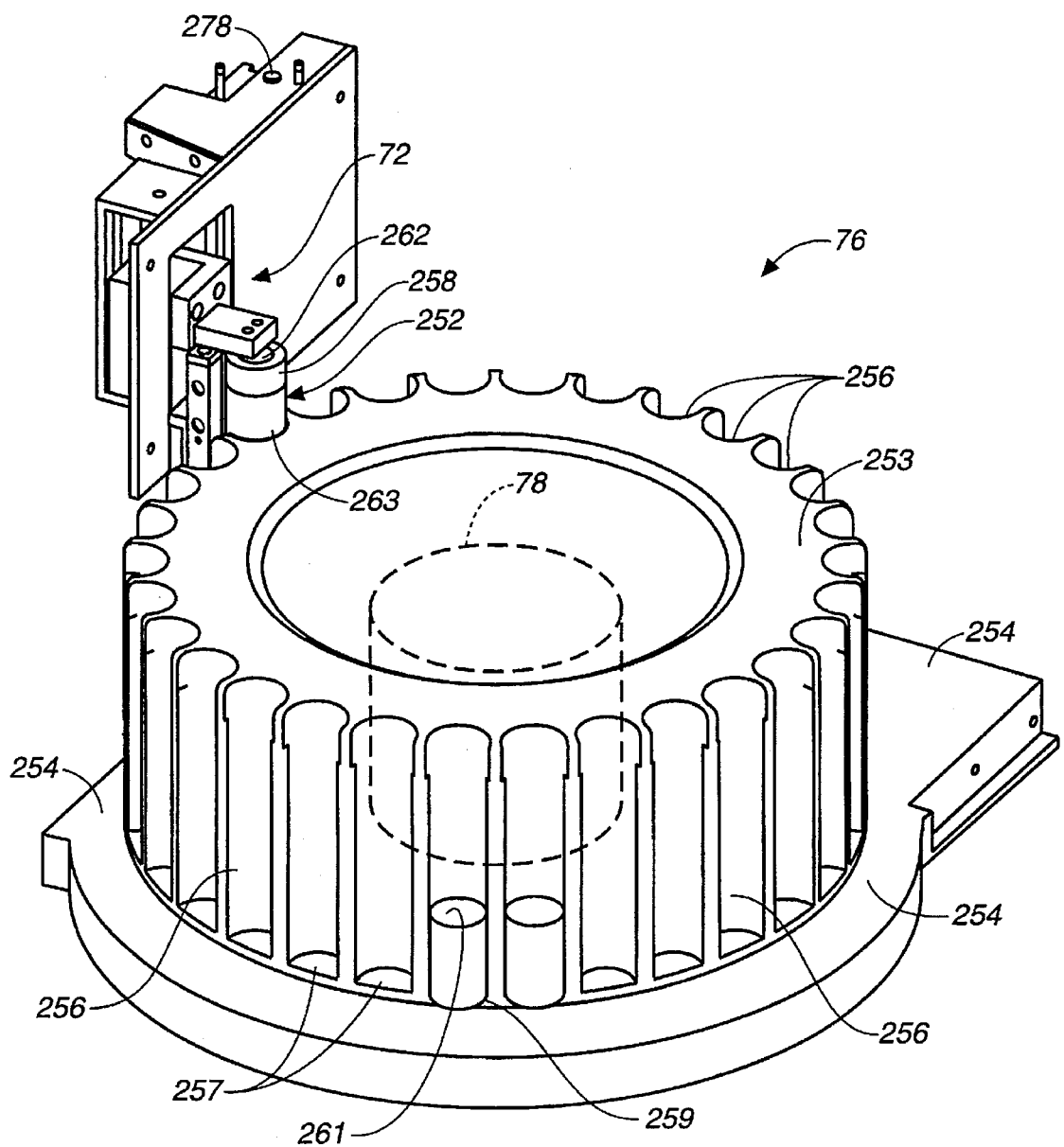
FIG._8

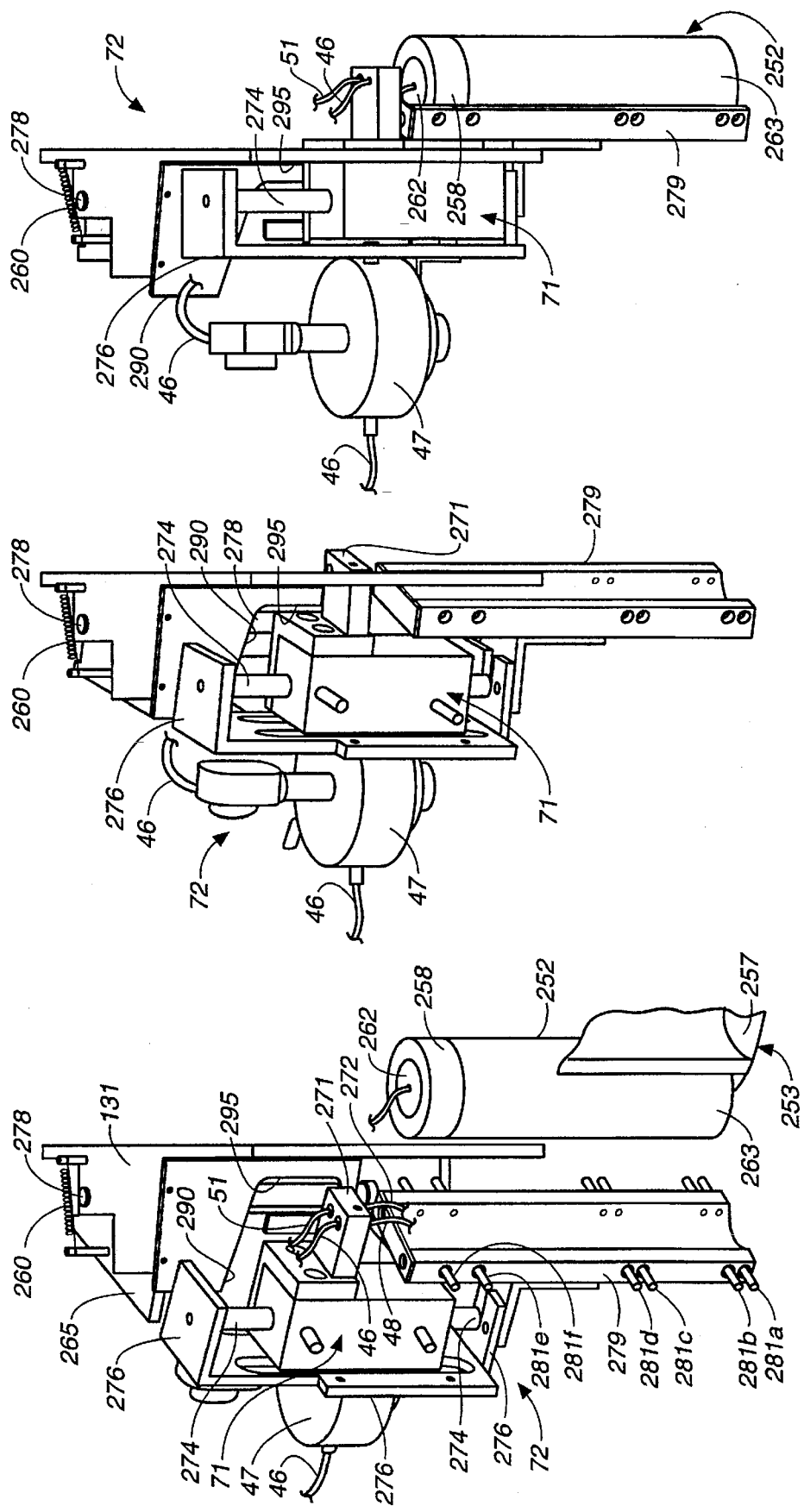

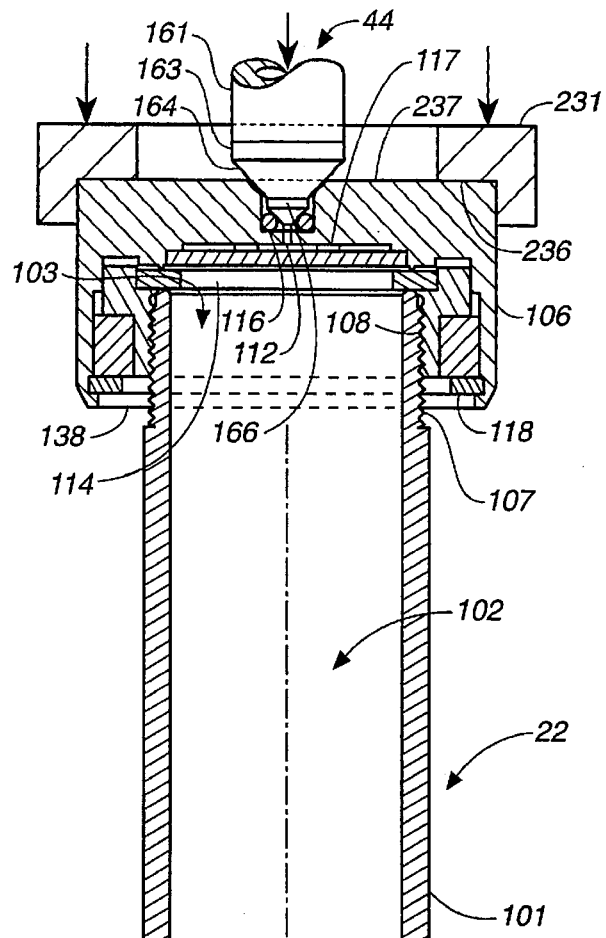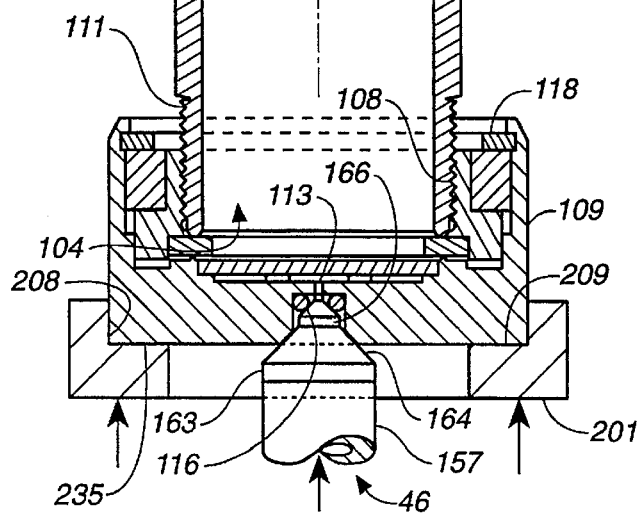
FIG._10

AUTOMATED ANALYTE SUPERCRITICAL FLUID EXTRACTION APPARATUS

RELATED APPLICATION

This application is a continuation-in-part application based upon co-pending parent application Ser. No. 08/259,667, filed Jun. 14, 1994 for "Accelerated Solvent Extraction System."

TECHNICAL FIELD

The present invention relates, in general, to a method and apparatus for extracting analytes from a sample, and more particularly, relates to an apparatus and method for solvent extraction or supercritical fluid extraction of organic analytes from a solid matrix sample under elevated temperatures and pressures.

BACKGROUND ART

The extraction of various analytes from solid matrix samples using a fluid under elevated temperatures and pressures sufficient to cause the fluid to be in a supercritical condition is well known and has been in use for many years. Carbon dioxide, for example, is a commonly employed material for supercritical analyte extraction. The carbon dioxide will be held in a container or cell which is raised to a temperature and pressure which causes the carbon dioxide to operate as a supercritical fluid. While in the supercritical conditions, the fluid is forced through a porous sample to cause extraction of analytes from the sample. A wide range of samples and analytes are amenable to such supercritical extraction techniques.

It also has been found that the addition of a solvent to a supercritical fluid, in relatively low percentages, for example, 10% or less, will enhance the supercritical extraction process. While supercritical fluid extraction, with solvent augmentation, enhances the supercritical fluid extraction result, the temperatures and pressures at which the fluid is maintained in supercritical condition are greater than would be optimum for a pure solvent extraction.

Accordingly, it has been recently discovered that a highly effective solvent extraction process for the extraction of organic analytes from a solid matrix sample can be accomplished by maintaining an organic analyte in contact with a non-aqueous organic solvent system in an extraction cell under temperatures of pressure below supercritical conditions. This process is described in detail in commonly owned, parent U.S. patent application Ser. No. 08/259,667, filed Jun. 14, 1994, and entitled "Accelerated Solvent Extraction System," which application is incorporated herein by reference in its entirety.

While solvent extraction at elevated temperatures below supercritical conditions has been found to be highly advantageous, it further is highly desirable to provide a method and apparatus for automatic operation of such a solvent extraction process. Moreover, for applications in which supercritical fluid extraction has advantages over a solvent extraction process, it is desirable to have an apparatus and method for automating the supercritical fluid extraction process.

There are commercially available apparatus for automating the supercritical fluid extraction process, but such systems have had disadvantages in the cells employed, their sealing schemes and the physical manipulation of cells and collection vials. Such apparatus do broadly include, however, cell storage trays, oven assemblies, extraction fluid communication assemblies and devices for moving the respective components in an automated sequence.

Accordingly, it is an object of the present invention to provide a method and apparatus which is suitable for automated analyte extraction using a solvent extraction process or a supercritical fluid extraction process which employs enhanced component handling and cell sealing structures that increase operational safety and reduce contamination potential.

Another object of the present invention is to provide an automated analyte extraction apparatus and method which allows high temperature and high pressure extractions to be automatically accomplished rapidly and with minimal technician supervision.

A further object of the present invention is to provide an automated analyte extraction system which is durable, low in cost, easy to maintain, will accommodate samples of various size, and is suitable for single or multiple cycle extractions.

DISCLOSURE OF INVENTION

The automated extraction apparatus of the present invention is useful in implementing either a solvent extraction process or a supercritical fluid extraction process in which an analyte is removed from a sample, such as a solid matrix sample, positioned in the cavity of a sample containment cell.

In one aspect of the present invention the present apparatus is comprised, briefly, of a loading tray formed for support of at least one cell, an oven assembly mounted proximate the tray and formed for heating of the cell and a sample contained in the cell, a fluid communication assembly mounted proximate the tray and including an inlet conduit and an outlet conduit formed for selective fluid coupling to a fluid passageway structure in the cell for communication of an extraction fluid to and from the sample-containing cavity. The fluid communication assembly is further formed to produce an elevated pressure of the extraction fluid while in the cavity of the cell. The apparatus further comprises a cell manipulation assembly mounted proximate the tray which carries the inlet and outlet conduit of the fluid communication assembly and is formed to move the inlet and outlet conduit into engagement with the cell to fluid couple the inlet conduit and the outlet conduit to the passageway structure of the cell and to simultaneously thereby grip the cell between the inlet and outlet conduits. The cell manipulation assembly further is formed to move the cell as gripped by the inlet conduit and the outlet conduit between the tray and the oven assembly, and the apparatus also includes a controller coupled to the cell manipulation apparatus and the fluid communication apparatus for control of fluid coupling and uncoupling with the cell, and for control of movement of the cell into and out of the oven assembly, and for control of communication of extraction fluid to and from the sample, and for control of the pressurization of the extraction fluid in the cavity.

In another aspect of the present invention, the present apparatus comprises, briefly, a cell support structure, a sample containment cell mounted in the cell support structure and having a body defining a sample-receiving cavity, a removable cap mounted to an access opening in the body to the cavity, a passageway extending through the cap to the cavity for the flow of an extraction fluid through the cap to the cavity, a cap seal assembly positioned between the body and the cap to seal the cap to the body upon application of inward force to the cap and a passageway sealing assembly carried by the cell proximate the passageway. A fluid communication assembly also is provided which is mounted proximate the cell support structure and formed for selective fluid coupling to and uncoupling from the fluid passageway for communication of an extraction fluid to and from the cavity and for producing an elevated pressure of the extraction fluid in the cavity. Finally, a manipulation assembly is mounted proximate the cell support structure and is formed to move a portion of the fluid communication assembly into sealed relation with the passageway sealing assembly carried by the cell for fluid coupling of the communication assembly to the passageway, and in the preferred form the manipulation assembly also urges a portion of the fluid communication assembly against the cap a tapered surface on the cap to automatically align and stabilize the cell and to apply an inward force to the cap to seal the cap against the cell body. Also in a preferred form, the cell support structure can be provided as an oven assembly including a clamping device formed in position to apply clamping force to the cap so as to enhance sealing of the cap against the cell body.

In a further aspect of the present invention, a process for extraction of an analyte from a sample is provided which is comprised, briefly, of the steps of displacing a fluid conduit assembly into sealed engagement with a passageway structure of a sample containment cell to simultaneously align, seal and grip the cell in a stable manner with the conduit assembly; while gripping the cell with the conduit assembly, moving the cell between a storage tray and oven assembly; causing flow of an extraction fluid from an extraction fluid reservoir to the cavity in the cell through the conduit assembly; elevating the pressure of the extraction fluid while the extraction fluid is in the cavity; heating the extraction fluid while at an elevated pressure; and thereafter purging the extraction fluid from the cavity through the conduit assembly to a fluid receptacle.

The process of the present invention also may be comprised of the steps of displacing a fluid conduit assembly into sealed engagement with a passageway structure of a sample containment cell while causing flow of an extraction fluid from a fluid reservoir to the cavity, elevating the pressure of the extraction fluid while in the cavity, and while the extraction fluid is at an elevated pressure, clamping a removable closure member provided on the cell while heating the extraction fluid using an oven assembly.

Finally, in a further aspect the process is comprised of the steps of displacing a fluid conduit assembly in a sealed engagement with a passageway structure in a sample containment cell to simultaneously seal the fluid conduit assembly to the cell and to seal a closure member for the cell to the body of the cell with the conduit assembly.

BRIEF DESCRIPTION OF THE DRAWING

FIG. 1 is a schematic representation of a flow diagram for the apparatus and method of the present invention.

FIG. 2 is a top perspective view of an apparatus constructed in accordance with the present invention with various components removed and the appearance panels removed for ease of illustration.

FIG. 3 is a top plan view, slightly enlarged, of the apparatus of FIG. 2.

FIG. 4 is a top perspective view of a containment cell tray and manipulation portion of apparatus of the present invention.

FIG. 5 is a top perspective view, somewhat enlarged, of an oven assembly constructed in accordance with the present invention.

FIG. 6A is a top perspective view of a cell manipulating arm assembly shown in an extended position for gripping of a cell from the tray assembly of FIG. 4.

FIG. 6B is a top perspective view of the arm assembly of FIG. 6A shown in the retracted position.

FIG. 7 is a fragmentary, top plan view of the apparatus of FIG. 2 with the cell manipulating carousel removed for illustration of the vial manipulating carousel.

FIG. 8 is a top perspective view of the vial manipulating assembly portion of the apparatus of FIG. 2.

FIGS. 9A, 9B and 9C are top perspective views of the outlet conduit manipulating assembly shown in a fully retracted position, an intermediate position and a position for deposit of fluid into a collection vial, respectively.

FIG. 10 is a side elevation view, in cross section, of a sample containment cell for use with the apparatus and process of the present-invention, showing also a portion of the oven assembly.

BEST MODE OF CARRYING OUT THE INVENTION

The method and apparatus of the present invention are particularly well suited for implementing rapid analyte extractions by using solvents at higher temperatures than conventional solvent extraction techniques and under pressures which, when combined with the elevated temperatures, are lower than supercritical conditions. The advantages of such solvent extractions are set forth in co-pending, parent U.S. patent application Ser. No. 08/259,667 and will not be repeated herein. The apparatus of the present invention is particularly well suited and designed for use with the elevated temperature and pressure solvent extraction method of the co-pending application, but it also may be used, or adapted for use, with conventional supercritical fluid extraction processes.

Referring now to FIG. 1, a flow diagram of the present apparatus is shown. The automated extraction apparatus, generally designated 21, is designed for use with a sample containment cell, generally designated 22, and shown in more detail in FIG. 10. The details of construction of cell 22 will be described only briefly in this application but are the subject of a commonly owned United States Patent application filed contemporaneously with this application and also incorporated herein by reference.

Automated extraction apparatus 21 further preferably includes a cell support structure or cell tray 23, in which cells can be stored or loaded for automatic handling. In some embodiments of the present invention, however, cell-tray 23 is optional. Similarly, it is preferable that solvent extraction occur at elevated temperatures, and it is necessary that supercritical fluid extraction occur at elevated temperatures. Accordingly, the present apparatus preferably includes an oven assembly, generally designated 24, which is mounted proximate tray 23 and is formed for heating of cell 22, and the sample positioned in the cell when the cell is placed in oven 24.

In order to communicate an extraction fluid to the sample for extraction of analytes therefrom, automated extraction apparatus 21 further includes a fluid communication assembly, which is comprised of a plurality of components. Briefly, the fluid communication assembly of the present invention preferably includes an extraction fluid reservoir 26 in which an extraction fluid 27, such as a solvent, is positioned. A pump 28 is coupled in fluid communication with reservoir 26, for example, through conduit 29. It will be understood, however, that pump 28 can be replaced by a high pressure source or other actuator which will cause flow of solvent 27 from reservoir 26 through conduit 29 to cell 22, as will be described in more detail below. The fluid communication assembly further preferably includes a pump valve 31 between conduit 32 and subconduits 33 and 34, which are connected to pump 28. It is possible to eliminate valve 31 and merely meter solvent flow by pump 28, which is preferably provided by a positive displacement pump in which each stroke produces a metered amount of fluid. Conduit 32 may have a pressure transducer 36 mounted therein which is operably electrically coupled to a controller, generally designated 37 (through electrical conductors, not shown) for the transmission of transducer signals to the controller. A check valve 38 and purge valve 39 can be provided in branch conduit 41 from the pump conduit 32 for use in a manner which will be described in more detail below. Similarly, a relief valve 42 can be provided in branch conduit 43 for relief of pressure in conduit 32 to waste receptacle 52 or atmospheric vent 55.

An end portion 44 of pump conduit 32 provides and acts as an inlet conduit to cell 22 for the flow of extraction fluid into the sample containment cell. Similarly, a conduit 46 also coupled to cell 22 acts as an outlet conduit from the cell and is part of the fluid communication assembly. Mounted in outlet conduit 46 is a static valve 47, the operation of which will be described in more detail below, and the end or needle portion 48 of outlet conduit 46 is received in a collection vial 252. In the preferred form, collection vial 252 is also vented by vent needle 272 and vent conduit 51 to waste receptacle 52 or directly to atmospheric vent 55.

Also included in the extraction fluid communication assembly can be the following additional elements, purge gas reservoir 53, with associated conduit 54, regulator 56 in branch conduit 57, which communicates through regulator 59 and on-off valve 58 with the reservoir 26 to optionally pressurize the solvent reservoir 26. Also optionally provided can be a relief valve 61 mounted in conduit 54 which terminates in a toggle valve 62, enabling toggling between a source of house air 63 and pressure reservoir 53, at the user's option in order to drive a pneumatic manifold, generally designated 64. Manifold 64, generally, is employed to control the various valves in the fluid communication assembly and to control the operation of various actuators comprising a manipulation assembly of the automated extraction apparatus 21 of the present invention.

Moving now to the components comprising the manipulation assembly, there are three actuators which are primarily concerned with cell manipulation in apparatus 21. First, pneumatic actuator or piston cylinder assembly 66 is coupled to move cell 22 between cell tray 23 and oven 24. Actuator 66 can be a double-acting piston and cylinder assembly controlled by valves 66a and 66b. Actuator 67 carries a portion of the fluid communication assembly, namely, inlet conduit 44 and outlet conduit 46, and moves the same into engagement with, and preferably sealed engagement with, cell 22. Pneumatic actuator or piston and cylinder assembly 68 is coupled to a cell clamping device schematically shown at 221 in order to clamp cell 22 while in oven assembly 24 for sealing purposes, which will be described hereinafter.

Broadly included in the expression manipulation assembly in extraction apparatus 21 of the present invention is a further actuator 71, which is coupled to displace outlet conduit needle 48 and vent conduit needle 272 carried in a common assembly 72 sometimes referred to as the "needle" assembly.

Finally, cell tray 23 preferably is movable and mechanically coupled at 73 to a motor 74, while vial tray 76 similarly is movable and coupled at 77 to a motor 78. Motors 74 and 78 are electrically connected to controller 37, by conductors which are not shown.

Referring now to FIG. 10, a sample containment cell 22 which is particularly well suited for use in extraction apparatus 21 is shown. Sample containment cell 22 has a body 101 which is preferably hollow and defines a sample-receiving cavity 102 therein. At least one opening, and in the form illustrated two end openings 103 and 104, are provided in cell body 101 in order to enable positioning of a sample from which an analyte is to be extracted in cavity 102. Removably mounted on the end of body 101 is at least one closure member or end cap 106, which is preferably threadably secured on threads 107 by a threaded insert member 108 carried by and secured to cap 106 by a retainer spring clip or ring 118. The opposite end cap 109 is constructed in a similar manner and threaded at threads 111 in the same fashion as cap 106, and accordingly will not be described in more detail herein.

Extending from an exterior of cell 22 to cavity 102 is a fluid passageway structure. In the preferred form, the cell fluid passageway structure provided by an inlet passageway or bore 112 and an outlet passageway or bore 113, each of which extend through end caps 106 and 109, respectively. Passageways 112 and 113 allow an extraction fluid to be injected or pumped into cavity 102 through inlet passageway 112 and out of the cavity through outlet passageway 113.

As the apparatus and process of the present invention are particularly well suited for solvent extraction at elevated temperatures and pressures, it will be appreciated that an important aspect of the present apparatus will be that the high temperature and high pressure solvent in cavity 102 must be contained. Leakage of such fluids can present a substantial safety hazard and can result in contamination of subsequent samples when multiple cells are sequentially processed using the apparatus of the present invention.

Accordingly, cell 22 preferably further includes a closure seal assembly, such as a deformable annular sealing washer 114, and a passageway sealing assembly 116, for example, in the form of a deformable O-ring. As will be seen, each end of cell 22 carries both the closure sealing assembly 114 and the passageway sealing O-ring 116.

Cell 22 also preferably includes an end frit or filter disk 117 which reduce channeling of the extraction fluid and prevent plugging of the outlet passageway 113.

It is most preferable that body 101 and end caps 106 and 109 be formed of a corrosive resistant material, such as stainless steel, which material also is effective in containing pressures at elevated temperatures. It will be understood, however, that other cell materials may be preferable, depending upon the operating temperatures and pressures, as well as the solvent employed in the apparatus and process of the present invention.

Fluid Coupling To Cell

In a first important aspect of the apparatus and method of the present invention, the sample containment cell 22 must be fluid coupled to the fluid communication assembly for delivery of an extraction fluid 27 to cavity 102 in the cell.

Referring now to FIGS. 2, 4, 6A and 10, fluid coupling of cell 22 to the fluid communication assembly can be described.

As will be seen in FIG. 2, apparatus 21 preferably is implemented by rotatably mounting two turntables or carousels 23 and 76 to the framework 131 of the apparatus. An upper carousel or turntable provides cell tray 23, which is best shown in FIG. 4. The cell tray assembly 23 can include a support member 132 which is coupled by fasteners or the like to a portion of framework 131. A rotatable turntable plate 133 is mounted on a spindle (not shown) which is coupled at opening 134 to a motor schematically represented in dotted lines as cell tray motor 74. The cell tray motor 74 is enclosed in an appearance housing above the cell tray.

As will be seen, the cell tray preferably includes a plurality of cell-receiving support bays 136 having upwardly facing shoulders 137 dimensioned to pass under and support a downwardly facing shoulder 138 (FIG. 10) on cell 22. Accordingly, motor 74, which can be a stepping motor or the like, is coupled by a shaft to rotate cell tray 23 so as to sequentially position cells 22 at an indexed location for fluid coupling to the fluid communication assembly of the present invention.

One of the highly desirable features about the construction of cell tray assembly 23 is that each of the loading bays 136 is constructed so as to support cells 22 of differing length. Since in each case cell 22 is supported by surface 138 on end cap 106 (or a corresponding surface on cap 109 if the cell is inverted), cell tray bays 136 will accommodate, for example, 11, 22 and 33 milliliter size cells. The cell length should not reach down to support member 132. The upper end of the cell will, in each case, be in the same height position for fluid coupling to the fluid communication assembly.

Referring now to FIG. 6A, the apparatus of the present invention which produces fluid coupling of the fluid communication assembly to cell 22 can be described. Fluid coupling assembly, generally designated 141, includes actuator 67, which may advantageously take the form of a double-acting piston and cylinder assembly coupled by pneumatic conduits 142 through a switching valve 143 (FIG. 1) to pneumatic control manifolds 64. In the assembly, piston rod 144 is stationary and fixed at 146 to the upper assembly arm member 147. As air is switched by valve 143 from one side to the other of piston 144, the cylinder housing 148 is reciprocated on guide rods 149 and 151 in an upward or downward direction. The guide rods are secured at upper ends 152 to the upper arm member 147 of the assembly frame and at the lower ends to a lower frame member 153.

Carried on reciprocating housing 148 is a lower arm 154 which extends outwardly and laterally to an end 156 that carries a rigid conduit 157 coupled to flexible conduit 158. Conduit 158 must accommodate movement of the lower arm by its own flexibility or a flexible joint, not shown.

The stationary upper arm 147 has an end 159 that carries a rigid conduit 161 that is fluid coupled to conduit 162. In the preferred form of the present invention, conduit 162 and rigid conduit 161 together comprise the fluid communication assembly inlet conduit, generally designated 44, which is in the fluid system as shown in FIG. 1. Similarly, the flexible conduit 158 and rigid conduit 159 together comprise the outlet conduit 46 of the fluid communication assembly.

As will be seen in FIG. 10, the end of the rigid conduits 161 and 157 each have mounted thereon a nozzle member 163 which is formed with a frusto-conical tapered surface 164 and an injector nose 166 having a central opening therein substantially corresponding in diameter to the diameter of cell passageway bores 112 and 113. As also will be seen from FIG. 10, the frusto-conical surface 164 mates with a similar conical recess in the caps so as to automatically cause cell 22 to come into alignment with nozzles 163 as the nozzles are driven into the cell caps by actuator 67. Moreover, the mating tapered or conical surfaces in the nozzle and cap provide gripping stability for movement of the cell, as is set forth below.

Operation of the actuator to effect fluid coupling can now be described. Since upper cap 106 is always at the same height as it is brought to the fluid coupling assembly 141 by rotatable carousel 23, the upper arm 159 may be fixed and rigid conduit 161 extend down by an amount which barely clears the top surface of cap 106. The cap, as supported by shoulder 138 on shoulder 137, with the cell depending therefrom, can therefore be rotated by tray 23 freely under conduit 161, which clears the outermost portion of the carousel as it rotates. When tray motor 74 rotates a selected bay 136 into substantial alignment with the stationary inlet conduit 161, the motor is stopped. While carousel 23 is rotated, arm 154 with movable outlet conduit assembly 46 is in a lowered position, which is sufficiently below end cap 109 for the longest of the cells which can be placed in carousel 23, that it will clear the lower end cap. Once the carousel is indexed, valve 143 can be switched to drive arm 154 upward until the rigid conduit 157 of the outlet conduit assembly 46 engages cap 109. As tapered surface 164 engages a mating tapered surface in cap 109, the cell tends to come into precise axial alignment with the lower nozzle 163. The fluid actuator 67 continues to drive movable housing 148 and arm 154 upward, carrying outlet conduit assembly 46 upward and seating lower nozzle 163 in the frusto-conical recess in cap 109. Lower nozzle 163 and conduit 157 begin to lift the cell slightly off shoulder 137 so as to drive the cell upwardly into the upper nozzle 163 of the inlet conduit assembly 44. The tapered surface on the upper nozzle 163 similarly aligns and seats against the mating tapered surface in cap 106.

In the preferred form, actuator 67 continues to drive the lower or outlet conduit assembly 46 upwardly until the protruding noses 166 are driven into deformable passageway seals 116 carried by the upper and lower cell caps. The passageway seals are deformed into sealing engagement with noses 166 in both inlet conduit 44 and outlet conduit 46. Thus, cell manipulating actuator 67 is formed to move at least one of the inlet conduit 44 and the outlet conduit 46 into engagement with cell 22 to fluid couple the inlet conduit and outlet conduit to the passageway structure of the cell, namely, bores 112 and 113. In the preferred form, this engagement is a sealing engagement in which the cell manipulating assembly effects sealing between the nozzle on inlet conduit rigid tube 161 with end cap 106 and the sealing assembly 116 carried thereby. Similarly, in the preferred form, the outlet conduit nozzle is driven into sealing engagement with the seal 116 carried by end cap 109.

One of the advantages of the apparatus of the present invention is that the sealing assemblies 116 are carried by the cap, rather than by the fluid communication apparatus. If a sealing assembly should fail, only the particular cell involved will be at risk and the likelihood of contamination will be lessened. The next cell in carousel 23, for example, may have perfectly good passageway structure seals 116 and the failure of preceding passageway seal assembly will not require shutdown of the present apparatus.

As will be appreciated, one method of controlling actuator 67 is by monitoring the fluid pressure with a pressure transducer so as to sense when lower movable arm 154 has produced sealing engagement of the assembly with cell 22. In the present invention the fluid pressure supplied to actuator 67 is merely left on so as to apply a maximum designed force to conduits 44 and 46, and the vertical position of housing 148 during reciprocation can also be sensed using optical sensing means. For example, an optical sensor support panel 171 can be mounted between stationary upper arm member 147 and stationary lower arm member 153 by mounting screws or fasteners 172. Carried by panel 171 are a plurality of optical sensors 173a, 173b and 173c (best seen in FIG. 6B) which sensors are electrically connected by conductors (not shown) to controller 37. Mounted to the back surface of movable actuator housing 148 is a Z-shaped flange 174 (FIG. 6B) which has an outer leg (not shown) which passes between the two sides of the optical sensors 173a, 173b, and 173c. As actuator housing 148 reciprocates vertically, therefore, the flange of member 174 passes through optical sensors 173a, 173b, and 173c to indicate the position of housing 148 and thereby enable controller 37 to sequence the fluid flow to sealing of the conduits to cell 22, depending upon the cell height. Panel 171 can have the sensing cells fixed thereto or they can be movably mounted to the panel, and controller 37 can be responsive to signals received from sensing cells 173a, 173b, and 173c to sense the position of the movable conduit arm 154.

As will be described in more detail below, the cell manipulating assembly 141 of FIG. 6A also preferably is mounted for rotation by a shaft 181 in bushings or bearings provided in fixed upper arm 147 and fixed lower arm member 153. This shaft 181 is best seen in FIG. 6B. The sensor panel 171, therefore, can also include a sensor 182 which is turned by 90 degrees relative to sensors 173a and is also an optical sensor electrically connected to controller 37 by conductors which are not shown. Sensor 182 can be used to sense the presence or absence of a flange member which is stationary or unmovable relative to framework 131 so as to provide feedback to the control as to the angular position of the entire assembly 141.

Transport Of Cell Assembly

In the preferred form of the apparatus of the present invention, cell assembly 22 is not only filled with fluid by the fluid communication assembly and thereafter pressurized, in a manner which will be described below, but it is also heated by an oven assembly 24. In a simplified form of the apparatus of the present invention, sample containment cell 22 can be manually placed directly in an oven assembly or other cell support structure. The fluid communication assembly can then be brought into fluid coupling with the cell assembly, as above described. This would be the case, for example, if FIG. 6A were surrounded by an oven. In the preferred form, however, an oven assembly is positioned proximate the cell supporting structure or tray 23 and the cell assembly is transported from the tray to the oven for elevation of the extraction fluid inside the cell assembly to enhance extraction effectiveness. Accordingly, in the preferred form of the invention, the apparatus cell manipulating assembly is formed for the movement or transport of cells from tray 23 to oven 24.

It is an important feature of the apparatus of the present invention, however, that transport or movement is accomplished by gripping cell 22 between inlet conduit 44 and outlet conduit 46 and then moving the cell, as gripped by the inlet and outlet conduits, between the tray and oven. Thus, in the preferred form, the cell manipulation assembly is formed to move at least one of the inlet and outlet conduits into engagement with the cell to fluid couple the cell to the fluid communication assembly and to substantially simultaneously grip the cell between the conduit ends. The cell manipulation assembly further is formed to move the cell as gripped between the inlet and outlet conduit between the tray and oven assembly.

In FIG. 6A assembly 141 has fluid coupled the fluid communication assembly to cell 22 while the cell is positioned substantially at a loading station or area at the carousel or tray 23. This is the position of arm assembly 141 in FIG. 2. In FIG. 6B the arms 147 and 153 have been rotated in a counterclockwise direction from FIG. 6A to a position at which cell 22 will be surrounded by the oven. This moved or oven position is also shown in FIGS. 3 and 4.

Accordingly, in the present invention the cell manipulation assembly is used to produce a fluid coupling and is further used to grip the cell in a stable condition between the frusto-conical conduit noses 163 and transport it between a support, such as carousel tray 23, to a proximate heating device, such as oven assembly 24. When the cell is inserted in the oven by pivoting of assembly 141 about shaft 181, the cell will still be fluid coupled to the fluid communication assembly portion of apparatus 21. Thus, as fluid coupled, extraction fluid can be communicated to cavity 21 of the cell and the cell simultaneously heated. Moreover, the pressure inside cavity 102 can be elevated so that the combination of elevated temperature and pressure increases the effectiveness of analyte extraction.

As best may be seen in FIGS. 3 and 6B, shaft 181 is coupled by mounting block 191 to the housing framework 131 so that articulation between the positions of FIGS. 2 and 3 can be accomplished by displacement of assembly 141. The rotatable displacement of assembly 141 about shaft 181 is driven by actuator 66 (FIG. 1) which can be coupled to any portion of assembly 141 which is not vertically displaced, such as the upper arm 147, and be supported by a stationary portion of frame 131. Again, the sensor 182 senses the angular position of assembly 141. In the most preferred form, actuator 66 will drive or rotate assembly 141 from the loading station at the cell to the oven station or heating station inside the oven and further overdrive slightly so that the side walls of body 101 of the cell are in contact with portions of oven 24 for conduction heating of the cell.

This is not an absolute requirement in that the oven assembly can operate as a radiation and/or convection heater, but heat transfer is improved by overdriving the rotation of assembly 141 into oven 24 until the body and/or end caps of the cell are engaged with the oven.

Oven Assembly

In the apparatus of the present invention, the preferred form of oven assembly 24 is shown in FIG. 5. The oven has a generally U-shaped metal body 201 which is elongated and open to one side 202 for pivotal receipt of cell 22 into the oven. Mounted in bores extending longitudinally in oven 24 is at least one resistance heater or thermal cartridge 203. In the preferred embodiment two cartridges 203 extend over substantially the entire length of oven body 201 and are coupled by electrical conductors 204 to a source of electricity which is controlled by controller 37. Mounted in between thermal resistance heating cartridges 203 is a temperature sensor 206 which is electrically connected to provide sensing signals through conductors 207 to controller 37. As will be seen, the interior of U-shaped body 201 preferably is formed with notches 208 dimensioned to slidably receive the top and bottom caps 106 and 109 of cells of varying lengths. The notches 208 are dimensioned for sliding receipt of the cell caps therein, but the upwardly facing surfaces 209 of the lower three notches 208 are intended to engage the downwardly facing surface of the lower cap 109, in a manner which will be described in more detail hereinafter.

It is preferred that oven assembly 24 include an outer insulated housing 211 which substantially encloses the oven body and includes an open side 212 to which a displaceable door structure, such as brush bristles 213, are mounted. A similar bristle assembly preferably covers the top opening 214, but is not shown for simplicity of illustration. Accordingly, as transport or cell manipulation assembly 141 rotates cell 22 into the oven, the cell displaces brush bristles 213 which then spring back to close or reduce the heat transfer out the open side and open top of the oven. As will be seen from FIG. 3, the upper arm 159 of assembly 141 essentially covers the upper opening on the top of oven 24, while the lower arm 154 reaches into the oven from the side, such that the bottom of the oven may be substantially closed and does not require a brush or other door closure. As will be appreciated, other forms of doors or closure on oven 24 are suitable for use with the present invention.

A further important feature of the present invention is that oven assembly 24 includes a cell clamping device or assembly 221. As can be seen from FIG. 5, oven assembly 24 is mounted on two vertically extending side-by-side post assemblies 220. Each of post assemblies 220 may advantageously formed as an elongated tubular sleeve member 222 in which a pair of rod members 223 are slidably telescoped. The bottom ends 224 of sleeves 222 rest on a member 226 which is attached to an actuator piston 225 of compression or clamping actuator 68. The upper end 227 of sleeves 222 bears upon an outward laterally extending ear 228 which is fixedly secured to oven body 201. Posts 223 extend slidably out through a bearing end ear 228 and up through an upper pair of ears 229 to an uppermost clamping member 231. The upper ends of rods or posts 223 are secured by nuts or the like 232 to the clamping member 231.

In operation, when actuator 68 is pressurized by controller 37 and pneumatic manifold 64, piston 225 is driven upwardly and carries sleeves upwardly on posts 223. The lower ends of posts 223, not seen, are secured to stationary plate 233 that is fastened at 234 to the stationary portion of actuator 68. Accordingly, the piston displacement causes the sleeves to rise while the posts 223 are held in position. As sleeves 222 rise on posts 223, they carry ears 228 which are attached to the oven body upwardly towards the upper clamping member 231. The intermediate ears 229 provide guidance to avoid misalignment.

As schematically may be seen in FIG. 10, the upwardly facing ledge or surfaces 209 in the lowermost notch 208 of the oven assembly engages the oppositely facing surface 235 on lower cap 109. Conversely, the downwardly facing surface 236 of upper clamping member 231 engages the upwardly facing surface 237 of the upper cap 106.

As the oven body 201 is driven upward by clamping sleeves 222, therefore, an axial clamping force is applied on each end cap 106 and 109 in an inward direction toward cavity 102. This oven inwardly directed clamping force, in turn, tends to drive each end cap or closure member against the seal assemblies 114 between the cap and cell body 101. As will be seen from FIG. 10, the end surfaces of body 101 make a face contact with sealing gaskets 114 and the oven clamping assembly augments or enhances this seal between the removable end caps and the cell body.

Additionally, it is a very important feature of the present invention that up as many as three separate clamping forces may be applied which tend to clamp the end caps 106 and 109 against the annular seals 114 and the seals against the annular ends of the cell body 101. First, as just described, the clamping forces in oven 24 apply an inward force to each end cap which drives the end cap toward the seal and toward the cell body.

Second, and independent of the clamping force in the oven clamping assembly 221, actuator 67, which drives inlet conduit 44 and outlet conduit 46 into sealed engagement with the end caps, also applies an axial inward force on the end caps toward seals 114. This inward sealing force would be present even if there were no oven clamping device. Third, the threadable mounting of end caps 106 and 109 on body 101 allows an inward axial force to be applied to the seals by simply finger-tight screwing the end caps down on the cell body. As will be seen in FIG. 10, the threads will permit tightening beyond the thickness of seal assemblies 114. This finger-tight sealing of the end caps similarly does not require an oven clamping device, or for that matter the conduit gripping of the cell.

The three inward force-producing structures have the following relative effect on sealing cavity 102. By applying the conduit pressure required to seal the inlet and outlet conduits to the passageways through the cap, the cell 22 can withstand a pressure in cavity 102 of about 100–200 psi. Finger-tight screwing of end caps 106 and 109 down on body 101 will allow the internal pressure in cavity 102 to be raised to about 1500 to 2000 psi. The cell clamping device allows the pressure in cavity 102 to be raised to as high as 3000 to 4000 psi.

One of the important features and aspects of using a fluid actuator 67 to drive conduits 44 and 46 into sealed relation with the end caps is that if runaway pressure should build up in cavity 102, the maximum pressure which can be applied by actuator 67 can be limited to a pressure below a pressure which cell body 101 can withstand. Accordingly, if the pressure inside cavity 102 exceeds the maximum pressure at which conduits 44 and 46 can be driven against passageway 116, what occurs is that the excess pressure in cavity 102 will blow out or blow by conduits 44 and 46 by backing them out of the cap recesses. While this creates a certain messiness, it is highly desirable as compared to rupturing cell body 101, and it provides another failsafe feature for the present apparatus.

Returning to FIG. 5, it is preferable that actuator 68 not be a double-acting cylinder and that a biasing spring be provided to return the sleeves and piston to the lowered position. Thus, a compression coil spring 241 can be mounted around each of posts 223 between the upper ears 229 and the clamping member 231. When the actuator pressure is dropped by valve 242 (FIG. 1) springs 241 will return the clamping device to an open position and permit removal of cell 22 from oven 24. As can be seen from FIG. 1, valve 242 is mounted in a branch conduit 243, which branches off of conduit 57 from compressed gas reservoir 53. It would be possible to run oven clamping actuator 68 from manifold 64, but in the preferred form gas reservoir 53 is used to run actuator 68 because the force required to reach the maximum clamping pressure usually cannot be achieved through most house air supplies.

It is further preferable that the automated analyte extraction apparatus of the present invention include a collection vial rack assembly, generally designated 76 which best may be seen in FIGS. 2, 7 and 8. The collection vial assembly 76 is formed to support and manipulate a plurality of collection vials 252, which are to be positioned for receipt of extraction fluid 27 after it has been passed through cell 22 and out of outlet conduit 46. In the preferred form, collection vial assembly 76 includes a vial supporting rack or carousel 253 which can be rotatably mounted to a base structure 254 secured to the framework 131 of apparatus 21. Drive motor 78, schematically shown in dotted lines in FIG. 8, is mechanically coupled to drive turntable or carousel 253 and is electrically coupled to controller 37. Controller 37 can step motor 78 so as to bring each of collection vials 252 into an indexed relation relative to needle assembly 72, which positions the discharge needle 48 of outlet conduit 46 inside vial 252 and simultaneously positions vent conduit needle 272 of vent conduit 51 for communication with the inside of vial 252. Each of the rack bays 256 of carousel 253 is formed for receipt and support of vials 252 in a stable generally upright position. The bottom surfaces 257 of bays 256 provide the downward support for vials 252. The vials 252 are not supported by their caps 258, but instead by the bottom surfaces as they seat on bay surfaces 257. In order to accommodate collection vials of varying height and volume, insert plugs 259 can be mounted in bays 256 so that the upper surface 261 will support the bottom of a shorter vial with cap 258 at the same vertical elevation for delivery of extraction fluid thereto by needle assembly 72.

In the preferred form, collection vials 252 are constructed as is conventionally known in the industry. The caps 252 have a central open area which is covered by a rubber diaphragm 262. The bodies 263 of the collection vials are preferably transparent to an optical sensor, such as an infrared sensor, although the vials are often formed of a dark amber glass to minimize degredation of the extraction fluid by visible light. As can be seen from FIG. 1, it is preferable that both the discharge needle 48 and needle 272 of vent conduit 51 be inserted into collection vial 252 through diaphragm 262. This can be most advantageously accomplished by inserting both elements simultaneously by using needle assembly 72.

FIGS. 9A through 9C illustrate the sequence of movement of needle assembly 72, as it is moved from a retracted position shown in FIG. 9A to a fully installed position shown in FIG. 9C.

In the preferred form, the end of outlet conduit 46 is coupled to a movable arm 271 which is mounted for both rotation about a vertical axis and vertical displacement. Similarly, vent conduit 51 is carried by arm 271, and each of these conduits are coupled to hollow fluid transmitting needles 48 and 272. Arm 271 extends laterally outwardly of, and is fixed for movement with, vertically displaceable member actuator 71, which is reciprocably mounted on piston shaft 274. The actuator piston is anchored to C-shaped bracket 276. Needle assembly actuator 71 is a double-acting actuator having control valve 277 (FIG. 1).

As best may be seen in FIG. 7, a roller-type follower 280 is mounted on a back side 285 of actuator 71. Positioned proximate follower 280 is a downwardly facing, sloping cam surface 290 (FIGS. 9A–9C) which terminates in a vertically extending cam surface 295. When actuator 71 is raised on piston 274, cam follower 280 is driven up into cam surface 285. The upward incline of surface 285 produces pivoting of bracket 276 and arm 265 on which it is mounted in a clockwise direction about axle 278 against tension spring 260. This brings the assembly to the FIG. 9C position.

To insert needles 48 and 272 into vial 252, the controller switches valve 277 and spring 260 rotate arm 265 and bracket 276 in a counterclockwise direction. Follower 280 follows downwardly sloped cam surface 290 and, that together with pressure on the other side of the piston, causes actuator 71 to fall and needles 48 and 272 to be positioned just over the diaphragm 262.

As the assembly reaches the position of FIG. 9C, follower 280 reaches vertical cam surface 295 and continued pressure on the bottom side of the piston drives the needles down through diaphragm 262 to the final position of FIG. 9C.

To withdraw the needles, the pressure is applied to the top side of the piston and actuator 71 is raised until roller follower 280 engage the cam surface 290, at which point the needles have cleared diaphragm 262 and the slope causes rotation in an opposite direction.

Also mounted on framework 276 is a vial-receiving channel 279 formed to mate with a side of the vial body. Channel 279 carries a plurality of optical emitters 281a–281f, which communicate a sensing beam through orifices in shell 279 and through the body 263 of collection vial 252 to the opposite side of the shell where the beam is received. The optical sensors 281a–281f are electrically connected to controller 37 by electrical conductors (not shown) as are the corresponding detectors on the opposite side of shell 279.

In operation, the needle subassembly is out of aligned position with vial 252 until the vial is brought to an indexed relation to the needle assembly. When controller 37 senses that motor 78 has driven the selected vial 252 to the indexed position, needle assembly 72 rotates in a counterclockwise direction as shown in FIGS. 9A–9C toward vial 252.

As the framework is rotated about axle 278 in the counterclockwise direction to the position of FIG. 9C, actuator 71 drives needles 48 and 272 through rubber diaphragm 262 and into collection vial 252 for communication of extraction fluid from cell 22 to vial 252.

Extraction Process

Having described the preferred embodiment of the extraction apparatus of the present invention, operation of the apparatus and implementation of the process of the present invention can be described in detail. The description will be in terms of the preferred embodiment, which includes a plurality of extraction cells, which are sequentially moved through the extraction apparatus with fluid being sequentially collected in a plurality of collection vials. It will be understood, however, that the present apparatus can be used with a single sample containment cell and a single collection receptacle.

The first step is to fill one or more cells 22 with the desired samples, usually in the form of a solid matrix sample, from which an analyte is to be extracted. The filling step is accomplished manually by unscrewing one of the end caps 106 and 109 on cell 22 and placing the desired amount of sample in cavity 102. Next, one or more cells 22 is installed in the cell tray or carousel 23 in the respective bays, where the cells are supported by their upper end caps 106. Similarly, a corresponding number of vials 252 are mounted in the collection rack or carousel 253 by a manual operation.

Next an extraction solvent, or in the case of supercritical fluid extraction, an extraction fluid 27, is placed in solvent reservoir 26 and a solvent reservoir coupled to conduits 57 and 29 of the fluid communication assembly. Using user input keyboard 291 in controller 37, the process of the present invention can be started. Motor 74 is actuated by controller 37 to rotate cell carousel 23 so as to index a selected one of cells 22 at a fluid coupling station for gripping and fluid coupling of the cell by the cell manipulating assembly 141. At the same time, controller indexes a corresponding collection vial 252 at an indexed position for coupling of outlet conduit 46 to the collection vial through needle assembly 72. The motion of the vial rack 76 or carousel 253 is controlled by motor 78 and controller 37. Once the cell and collection vial are appropriately positioned between the rigid inlet conduit end 161 and the rigid outlet conduit end 157, the controller operates actuator 67 so as to cause the outlet conduit 157 to be driven up into the bottom cell cap 109 so as to fluid couple the cell to the fluid communication system of the apparatus and simultaneously grip the apparatus between inlet conduit 44 and outlet conduit 46. Once full gripping has been sensed through sensors 173a, 173b, or 173c, actuator 67 holds the cell between the inlet and outlet conduits. The cell is now slightly elevated with respect to turntable 23 and, therefore, free to be moved.

It should be noted that rigid conduit portions 157 and 161, in fact, surround the conduits 46 and 44 which pass concentrically therethrough to nozzles 163. These conduit portions are designed to provide the gripping strength necessary for gripping cell 22', which strength would not normally be present in the small diameter conduits 44 and 46, which are all that are required for the relatively low volumetric flow of the extraction solvent.

Next, controller 37 operates actuator 66 which rotates assembly 141 about shaft 181. Two independent valves 66a and 66b are provided so that the actuator can be stopped or parked in either the position next to the carousel 23 (at the end of each cycle) or the oven position. Actuator 66 drives assembly 141 from the position shown in FIGS. 2 and 6A to the position shown in FIGS. 4 and 6B, at which point the cell 22 is urged into contact with the oven for better heat transfer.

The angular position of assembly 141 can then be sensed by sensor 182 so that the controller 37 can tell when cell 22 is fully advanced into oven assembly 24.

With cell 22 in oven assembly 24, controller 37 now actuates oven clamping device 221. This is accomplished by operating actuator 68 against a spring biasing force by springs 241. The combination of cell threads, actuator 67 producing gripping between the end caps and clamping device 221 effectively seals end caps to cell body 101 as well as sealing inlet conduit 44 and outlet conduit 46 to the cell passageway structure. During the process of fluid coupling the cell to the fluid communication assembly and moving the cell by the fluid inlet and outlet conduits to the oven, the controller can also move needle assembly 72 from the retracted position to a position at which the needles 48 and 272 are driven down through the rubber diaphragm 262 and into collection vial 252.

Apparatus 21 is now ready for commencement of the extraction cycle or cycles.

Once both the cell and receiving vial are coupled for fluid communication of extraction fluid or solvent 27 through the system, controller 37 opens pump valve 31 and static valve 47 through the corresponding manifold valves 31a and 47a. As illustrated, pump 28 is a double headed pump for smoother fluid output but a single headed pump also may be used. Pump 28 is started and solvent 27 is drawn from reservoir 26, with the aid of a slight pressure head from gas source 53 through conduits 54 and 57. The solvent or extraction fluid is pumped through conduit 29 and one of conduits 33 or 34 to conduit 32, which terminates in the inlet conduit 44 inside rigid conduit portion 161, with nozzle 163 that injects solvent through inlet passageway 112 in cell 22.

The pump continues to operate until cavity 102 is filled with solvent and solvent begins to exit outlet passageway 113 and out the outlet conduit assembly 46 carried inside rigid conduit member 157. The exiting extraction fluid passes along conduit 46 to needle assembly 72 and begins to be forced out of needle 48 and into collection vial 252. When the extraction fluid in collection vial 252 reaches the first or lowermost optical sensor 281a, a signal is sent to controller 37 which closes the static or outlet valve 47.

It should be noted that during the pumping process the pressure in cavity 102 of the fluid will rise as a result of the resistance to flow through the cell produced by the small bores 112 and particularly bore 113. Additionally, the solid matrix material of the sample resists flow, as do the two frits mounted across the inlet and outlet passageways.

Accordingly, pressure has already begun to rise in cell 102 when static or outlet valve 47 is closed. The closure of outlet valve 47, however, produces a further rise in the cell, which is transmitted upstream to pressure transducer 36. The pressure transducer then sends signals to controller 37 as to the pressure in conduit 32 and thus cavity 102 of cell 22. When the pressure reaches a predetermined level, which can be input through keyboard 291 to controller 37, the controller maintains a pressure controlled valve using, as needed, incremental strokes of the pump.

In the preferred form of an assembly 24 will be operating at a predetermined elevated temperature, as controlled by signals from thermocouple 206 in the oven assembly. Accordingly, when cell 22 is moved from the cell tray 23 to heater assembly 24 it will enter the pre-heated oven and temperature will begin rising in the extraction fluid as soon as it reaches the cell. As will be appreciated, the rising temperature of the extraction fluid in cell cavity 102 can produce its own pressure rise in the cavity. Accordingly, as the extraction fluid temperature rises there is the possibility, and likelihood, that the pressure will exceed the target pressure for the cell, and if transducer 36 senses a pressure rise above the targeted or predetermined pressure, controller 37 will open static valve 47 for a short time so as to reduce the excess pressure in cavity 102. This pulsing of outlet valve 47 results in small quantities of extraction fluid passing through needle 48 to vial 252, but the quantities are very small as compared to the overall sample.

Through the use of gate valve 47, a substantial equilibrium temperature and pressure will be reached inside cavity 102 and the controller will allow this equilibrium condition to remain during a "soak" portion of the processing cycle of a predetermined length. The soak time can again be input at keyboard 291 so as to correspond to the desired extraction time for the particular matrix material in cavity 102. As will be understood, controller 37 will include a storable memory which can be programmed in a conventional manner so as to enable the soak time for each sample cell to be the same or different, as determined by the user.

Once the predetermined soak time at the desired temperature has been completed, the fluid communication assembly purges or flushes the extraction fluid in cavity 102 into collection vial 252. This is accomplished by opening outlet 47 to vial 252. The pump responds to the drop in pressure for a predetermined number of strokes. The pump is preferably a pneumatic, volume-displacement pump which causes a metered amount of solvent to enter line 32 and thereby be forced into cell cavity 102. Thus, the cell cavity 102 is flushed with a new aliquot of solvent and the solvent which has soaked in cavity 102 is expressed out outlet conduit 46 and needle 48 into collection vial 52.

At this point it is possible to withdraw needle assembly 72 from collection vial 252 by operation of the needle assembly actuator 71. Vial rack 76 can then be rotated by motor 78 and a new vial positioned for receipt of the second aliquot of solvent or extraction fluid.

Alternatively, the original collection vial 252 can remain in place for a second or repeat soak for a fixed length of time, which can be the same or different as the first soak. Again, the controller allows equilibrium in the pressure and temperature to be reached using static valve 47 and then soaks the sample for the second soak time. It will be appreciated that virtually any number of Solvent extractions soak cycles can be employed, although at some point the capacity of vial 252 will be exceeded and a second or third vial will have to be repositioned to receive the flushed out solvent after soaking.

At any time after the first soak, as programmed by the controller, apparatus 21 can purge or flush the extraction fluid from cavity 102 with an inert gas, rather than with additional solvent. The gas flush or purge process is accomplished by closing inlet valve 31, or disabling the pump opening outlet valve 47, and opening purge valve 39 so as to pressurize conduit 32 with a gas from reservoir 53. The gas advantageously can be nitrogen which will be driven in through inlet conduit 44 and passageway 112 to cell cavity 102. The flushing gas will then drive the extraction fluid from cavity 102 and from the matrix out through cell passageway 113 and outlet tubing or conduit 46 to collection vial 252. An advantage of the gas flushing or purge is that the solid matrix sample is also dried by the purge so that when inlet conduit 44 and outlet conduit 46 are uncoupled from fluid communication with cell 22, the cell does not drip extraction fluid from the outlet passageway 113. As above-noted, the gas purge can occur after the first soak or any subsequent soak, as determined by programing controller 37.

It should be noted that the second highest optical sensor 281b is positioned on the sensor shell 279 so as to communicate a signal to controller 37 when the fluid level reaches a desired height for collection vial 252, for example, one extraction cycle. An upper sensor 281e communicates a fluid presence signal to the controller, the controller will prevent further filling of collection vial 252 and automatically move to another collection vial. The uppermost sensor 281f on the sensor shell 279 is provided to sense the presence of a collection vial since it will be interrupted by the solid cap 258. Signals from sensor 281f, therefore, insures that the collection vial is present when the needle assembly is lowered so that extraction fluid is not pumped out of needle 48 when no vial is present. Intermediate sensors 281c and 218a can be used with shorter vials or to provide multiple cycle sensing.

Once the purge of extraction fluid to vial 252 has been completed, valve 39 is shut, allowing gas pressure in line 32 to return to open atmosphere pressure. Then valve 42, the relief valve, may be pulsed to assist in de-pressurizing line 32. Valve 68 allows oven clamping to disengage from cell, and then controller 37 operates actuator 66 through valve 66a to swing the cell gripping assembly 141 from the oven out to cell tray 23. Controller 37 thereafter operates valve 143 to drive double-acting actuator 67 in a direction uncoupling conduits 44 and 46 from the cell by dropping arm 154 downwardly away from the cell. Cell 22 then comes to rest on upwardly facing U-shaped shoulder 137 of the tray bays 136.

In the preferred form of the process, the controller also includes a rinse step in which the primary purpose is to remove any contamination in outlet conduit 46 and needle 48 which would corrupt a subsequent extraction sample. The rinse cycle can be accomplished by rotating cell tray 23 to a rinse cell mounted at a predetermined bay 136 in tray 23 using motor 74. Similarly, vial rack 76 can be rotated to a corresponding rinse station position for a rinse vial 252. The actuator 67 is then caused to fluid couple the inlet and outlet conduits with a rinse cell 22 and actuator 71 causes needle assembly 72 to be inserted into the rinse collection vial 252. For the rinse step, the rinse cell 22 does not need to be moved into oven assembly 24, and accordingly actuator 66 is not operated. The controller can instead simply open valve 31 or enable the pump 28 and valve 47 and operate pump 28 to pump a measured volume of solvent from reservoir 26 through the rinse cell, which has no sample in it and can have a reduced volume, so that the extraction fluid merely passes through the rinse cell to outlet conduit 46. Once a measured amount has been pumped through the outlet conduit, it will rinse the extraction analytes from the previous sample from outlet conduit 46 and needle 48 into the rinse collection vial 252. This cleans the apparatus downstream of cell 22 so as to prevent contamination of the next extraction fluid which is collected using the apparatus of the present invention. After the rinse of solvent through outlet conduit 46, it is preferably to close valve 31 and open valve 39 so that a nitrogen purge through the rinse cell and outlet conduit to the rinse collection vial can be accomplished. This pushes the remaining solvent into the collection vial and out of the outlet conduit 46.

In a typical loading of cell tray 23 and vial rack 76, there are four rinse cell stations and four rinse collection vials, with the remaining cells and remaining vials being used for samples and the collection of extraction fluid containing analytes.

At the end of the nitrogen purge of the rinse step, the purge valve 39 is closed and the automated extraction apparatus can then begin another sample extraction process by rotating the next sample cell 22 to the cell manipulation assembly 141.

What is claimed is:

1. An apparatus for automated extraction of an analyte from a sample positioned in a cavity of a sample containment cell having a fluid passageway structure in communication with said cavity, said apparatus comprising:

a loading tray constructed and arranged to support a cell having a cavity therein;

an oven assembly mounted proximate said tray and operable for heating said cell and said sample positioned in said cavity when said cell is positioned in said oven;

a fluid communication assembly mounted proximate said tray and including an inlet conduit and an outlet conduit constructed and arranged for selective fluid coupling to and uncoupling from a fluid passageway structure of said cell for communication of an extraction fluid to and from said cavity, said fluid communication assembly further being operable to produce an elevated pressure of said extraction fluid in said cavity;

a cell manipulation assembly mounted proximate said tray, said inlet conduit and said outlet conduit being carried by said manipulation assembly, and said manipulation assembly being constructed and arranged to move at least one of said inlet conduit and said outlet conduit into engagement with said cell to fluidly couple said at least one of said inlet conduit and said outlet conduit to said passageway structure and to substantially simultaneously thereby grip said cell therebetween in a manner permitting fluid communication to and from said cavity, and said cell manipulation assembly further being constructed and arranged to move said cell, as said cell is fluidly coupled and gripped between said inlet conduit and outlet conduit between said tray and said oven assembly; and comprising a controller coupled to said cell manipulation assembly and said fluid communication assembly for automatic control of fluid coupling and uncoupling with said cell, for control of the movement of said cell into and out of said oven assembly, for control of communication of extraction fluid to and from said sample in said cavity, and for control of the pressurization of said extraction fluid in said cavity.

2. The apparatus as defined in claim 1 wherein, said cell manipulation assembly urges said inlet conduit and said outlet conduit into, and maintains said inlet conduit and said outlet conduit in, sealed engagement with said cell.

3. The apparatus as defined in claim 2, and a cell structure having a passageway structure including an inlet passageway and an outlet passageway each communicating with said cavity, and said cell structure having a passageway seal assembly carried by said cell structure proximate each of said inlet passageway and said outlet passageway, said seal assembly being constructed and arranged to seal against said inlet conduit and said outlet conduit.

4. The apparatus as defined in claim 2 wherein, said fluid communication assembly includes an extraction fluid reservoir, said inlet conduit being connected to said reservoir, a pump operably connected to said controller operable to pump said extraction fluid from said reservoir to said cell, and an inlet valve operably connected to said controller and positioned in said inlet conduit operable for selective opening and closing to pressurize said cavity and permit extraction fluid to be pumped from said cavity.

5. The apparatus as defined in claim 4 wherein, said fluid communication assembly further includes an outlet valve positioned in said outlet conduit and operably connected to said controller to regulate pressure in said cavity and control the flow of extraction fluid through said cavity.

6. The apparatus as defined in claim 5, and a fluid collection vial positioned to receive extraction fluid from said outlet conduit downstream of said outlet valve.

7. The apparatus as defined in claim 4, and a fluid collection vial positioned to receive extraction fluid from said outlet conduit.

8. The apparatus as defined in claim 1 wherein, said cell manipulation assembly is operable to grip said cell between said inlet conduit and said outlet conduit proximate opposite ends of said cell.

9. The apparatus as defined in claim 8 wherein, said tray is constructed and arranged to orient said cell with a longitudinal axis of said cell in a near vertical orientation.

10. The apparatus as defined in claim 1 wherein, said tray is constructed and arranged to receive and store a plurality of cells therein.

11. The apparatus as defined in claim 10 wherein, said tray is mounted for movement; and said cell manipulation means is further operable to move said tray to position selected ones of said plurality of cells in indexed relation to said oven assembly for gripping between said inlet conduit and said outlet conduit.

12. The apparatus as defined in claim 11 wherein, said tray is a carousel mounted for rotatable movement.

13. The apparatus as defined in claim 11 wherein, said tray is constructed and arranged to receive and support cells of differing size in a position for movement between said tray and said oven assembly, and said tray is removably mounted to said apparatus.

14. The apparatus as defined in claim 13 wherein, said cell manipulating assembly is operable for pivotal movement of said cells between said tray and said oven assembly upon gripping of said cells between said inlet conduit and said outlet conduit.

15. The apparatus as defined in claim 1 wherein, said cell manipulating assembly displaces said inlet conduit and said outlet conduit toward and away from each other to grip said cell and to fluid couple said inlet conduit and outlet conduit to and uncouple said inlet conduit and said outlet conduit from said passageway structure of said cell.

16. The apparatus as defined in claim 1 wherein, said oven assembly is constructed and arranged to receive said cell through a displaceable oven door structure.

17. The apparatus as defined in claim 16 wherein, said door structure is provided by a brush assembly having displaceable bristles.

18. The apparatus as defined in claim 1 wherein, said oven assembly includes a temperature sensor coupled to said controller.

19. The apparatus as defined in claim 1 wherein, said oven assembly includes a movable clamping carriage and a support member, and said cell manipulation assembly is further operable to displace said movable clamping carriage relative to said support member between an open position, suitable for movement of said cell into said oven assembly, and a clamping position, applying a clamping force to said cell between said clamping carriage and said support member in a manner assisting a fluid-tight seal of said cavity.

20. The apparatus as defined in claim 19 wherein said apparatus is intended for use with a cell having at least one removable end cap providing access to said cavity for insertion of said sample into said cavity, and wherein, said clamping carriage and said support member clamp said cell between said end cap and an oppositely facing surface on said cell.

21. The apparatus as defined in claim 20 wherein, said clamping carriage is constructed and arranged to receive cells of varying size and urge said cells against said camping member.

22. The apparatus as defined in claim 1 wherein, said oven assembly is operable for conductive heating of said cell; and said cell manipulation assembly applies a positive force to said cell urging said cell into contact with said oven assembly.

23. The apparatus as defined in claim 1 wherein, said oven assembly is a U-shaped assembly formed with an open side dimensioned for movement of said cell into a position inside said U-shaped assembly, and said oven assembly includes at least one resistance heating element.

24. The apparatus as defined in claim 23 wherein, said oven assembly is constructed and arranged to receive and heat cells of varying size.

25. The apparatus as defined in claim 1, wherein, said fluid communication assembly further includes at least one fluid collection vial positioned for receipt of said extraction fluid from said cavity through said outlet conduit.

26. The apparatus as defined in claim 25, and a collection manipulation assembly mounted proximate said tray and constructed and arranged for receipt and storage of a plurality of collection vials, said collection manipulation assembly further being operably connected to said controller and operable for movement of one of said fluid communication assembly and a selected one of said plurality of collection vials into a position for a receipt of said extraction fluid from said outlet conduit.

27. The apparatus as defined in claim 26 wherein, said collection manipulation assembly includes a movable vial rack formed to receive and support said plurality of said collection vials therein.

28. The apparatus as defined in claim 27 wherein, said vial rack is provided by a rotatable vial carousel.

29. The apparatus as defined in claim 28 wherein, said collection manipulation assembly further carries a vent conduit of said fluid communication assembly, and said collection manipulation assembly moves said vent conduit between said retracted position and aid extended position for venting of said selected one of said collection vials.

30. The apparatus as defined in claim 29 wherein, said vent conduit is fluidly coupled to a one of a waste reservoir and a vent.

31. The apparatus as defined in claim 30 wherein, said fluid communication assembly further includes an extraction fluid sensor assembly positioned proximate said collection vial, said sensor assembly being operable to sense at least one of the presence of said collection vial and a level of said extraction fluid in said collection vial, said extraction fluid sensor assembly being operatively coupled to said controller for communication of sensor signals thereto, and said controller being responsive to said sensor signals to control the flow of said extraction fluid to said cell.

32. The apparatus as defined in claim 31 wherein, said extraction fluid sensor assembly is operable to sense a plurality of levels of said extraction fluid in said collection vial.

33. The apparatus as defined in claim 32 wherein, said extraction fluid sensor assembly is comprised of a plurality of optical sensors positioned to sense the level of said extraction fluid in said collection vial by passing an optical beam through said collection vial; and said collection vial is sufficiently transparent to said optical beam for sensing through said collector vial.

34. The apparatus as defined in claim 29 wherein, said collection manipulation assembly simultaneously moves said outlet conduit and said vent conduit into substantially sealed relation with said selected one of said collection vials in said extended position.

35. The apparatus as defined in claim 27 wherein, said collection manipulation assembly further carries said outlet conduit of said fluid communication assembly, and said collection manipulation assembly is operable for movement of said outlet conduit between a retracted position, out of fluid communication with said collection vials, and an extended position at which said outlet conduit is positioned for flow of said extraction fluid into a selected one of said collection vials while mounted in said movable vial rack.

36. The apparatus as defined in claim 1 wherein, said fluid communication assembly further includes a flushing assembly fluidly coupled for selective flow of a flushing fluid to said inlet conduit and said cavity, said flushing assembly including a source of flushing fluid and a valve assembly operably connected to said controller for movement of said valve assembly to produce selective flow of a flushing fluid to said cavity.

37. The apparatus as defined in claim 36 wherein,, said source of flushing fluid is provided by a reservoir of a gas under pressure.

38. The apparatus as defined in claim wherein, said fluid communication assembly includes a rinsing assembly fluidly coupled for selective flow of a rinsing fluid to said cavity and to said outlet conduit and operatively coupled to said controller.

39. The apparatus as defined in claim 1 wherein, said fluid communication assembly includes a pneumatic flow control manifold operatively coupled to said controller and provided with a plurality of solenoid-actuated valves operated by said controller and positioned to control fluid flow in said apparatus.

40. The apparatus as defined in claim 1 wherein, said controller is electrically powered and includes a user input, and a memory device having a sequence establishing program stored therein, said memory device further being programmable by said user input to change said sequence establishing program.

41. The apparatus as defined in claim 1, and a fluid collection cell having a central cavity dimensioned for receipt of a sample therein, said collection cell further being formed with at least one passageway structure communicating with said central cavity, and said collection cell being mounted in said tray.

42. The apparatus as defined in claim 41 wherein, said collection cell includes at least one removable cap member providing access to said central cavity for placement of said sample in said central cavity.

43. The apparatus as defined in claim 42 wherein, said collection cell includes a cap seal assembly constructed and arranged for sealing said cap by application of an inwardly directed force to said cap.

44. The apparatus as defined in claim 43 wherein, said cap member is threadably secured to said collection cell and provides a finger-tight structure for applying said force to said cap seal assembly.

45. The apparatus as defined in claim 44 wherein, said cell manipulating assembly is operable to grip said collection cell by said inlet conduit and said outlet conduit between said cap member and an opposed surface to apply an additional inwardly directed force to said cap member to augment sealing of said cap member.

46. The apparatus as defined in claim 45 wherein, said oven assembly includes a clamping structure operable to clamp said collection cell therein between said cap member and an opposed surface to apply still another additional inwardly directed force to said cap member.

47. The apparatus as defined in claim 41 wherein, said collection cell is further formed with a passageway sealing assembly formed for sealing of said inlet conduit and said outlet conduit to said passageway structure.

48. The apparatus as defined in claim 47 wherein, said collection cell has an elongated hollow body and removable end caps mounted to said body to define said central cavity, said collection cell further has inlet passageway in one end cap and an outlet passageway in the other end cap, and collection said cell has a pair of cap seal assemblies sealing each of said end caps to said body upon application of a sealing force thereto, and a pair of passageway sealing assemblies sealing positioned for sealing inlet conduit and said outlet conduit to said collection cell.

49. The apparatus as defined in claim 1 wherein, said inlet conduit and said outlet conduit are constructed and arranged to cooperate with surfaces on said cell to produce alignment of said cell with said inlet conduit and said outlet conduit as said cell manipulation assembly moves said inlet conduit and said outlet conduit into engagement with said cell.

50. The apparatus as defined in claim 49 wherein, said inlet conduit and said outlet conduit are each formed with tapered alignment surfaces which cooperate with mating surfaces on said cell.

51. The apparatus as defined in claim 50 wherein, said tapered surfaces are frusto-conical.

52. The apparatus as defined in claim 50 wherein, said tapered surfaces are constructed and arranged to cooperate with mating surfaces on said cell to stabilize said cell as gripped between said inlet conduit and said outlet conduit.

53. An apparatus for extraction of an analyte from a sample comprising:

a cell support structure;

a sample containment cell mounted in said cell support structure and having a body defining a sample-receiving cavity, a removable cap mounted to said cell over an access opening in said body to said cavity for positioning a sample therein, a passageway extending through said cap to said cavity for the flow of an extraction fluid through said cap, a cap seal assembly positioned between said body and said cap to seal said cap to said body upon application of an inward force to said cap, and a passageway sealing assembly carried by said cell proximate said passageway;

a fluid communication assembly mounted proximate said cell support structure and being operable for selective fluid coupling to and uncoupling from said fluid passageway for communication of an extraction fluid to and from said cavity, said fluid communication assembly further being operable to produce an elevated pressure of said extraction fluid in said cavity; and a manipulation assembly mounted proximate said cell support structure and operable to move a portion of said fluid communication assembly into sealed relation with said passageway sealing assembly carried by said cell for fluid coupling of said fluid communication assembly to said passageway;

an oven assembly mounted proximate said, cell support structure, said manipulation assembly being operable to move said cell between said cell support structure and said oven assembly with said cell being fluidly coupled to said fluid communication assembly; and comprising a controller coupled to said manipulation assembly and said fluid communication assembly for automatic control of the movement of fluid communication assembly into and out of fluid coupling with said cell, for control of the flow of extraction fluid to and from said sample in said cavity, and for control of pressurization of said extraction fluid in said cavity.

\* \* \* \* \*

UNITED STATES PATENT AND TRADEMARK OFFICE
CERTIFICATE OF CORRECTION

PATENT NO. : 5,660,727

DATED : August 26, 1997

INVENTOR(S) : GLEAVE et al.

It is certified that error appears in the above-identified patent and that said Letters Patent is hereby corrected as shown below:

Column 12, line 45, immediately following "oven 24", begin a new paragraph.

Claim 38, column 22, line 1, delete "claim wherein" and insert therefor --claim 1 wherein--.

Signed and Sealed this

Sixth Day of January, 1998

Attest:

BRUCE LEHMAN

Attesting Officer

Commissioner of Patents and Trademarks